United States Patent [19]
Kato et al.

[11] Patent Number: 5,972,671
[45] Date of Patent: Oct. 26, 1999

[54] FRUCTOSYL AMINO ACID OXIDASE AND PROCESS FOR PRODUCING THE SAME

[75] Inventors: Nobuo Kato, Kameoka; Yasuyoshi Sakai, Otsu; Yoshiki Tani; Masayuki Yagi, both of Kyoto; Fumiyo Funatsu, Hirakata, all of Japan

[73] Assignee: Kyoto Daiichi Kagaku Co., Ltd., Kyoto-fu, Japan

[21] Appl. No.: 09/030,442

[22] Filed: Feb. 25, 1998

Related U.S. Application Data

[62] Division of application No. 08/396,761, Mar. 1, 1995, Pat. No. 5,789,221.

[30] Foreign Application Priority Data

Mar. 3, 1994 [JP] Japan ........................... 6-33488

[51] Int. Cl.⁶ .............. C12N 9/06; C12N 9/04; C12N 9/02; C12N 1/14
[52] U.S. Cl. .......... 435/191; 435/190; 435/192; 435/189; 435/929; 435/256.5
[58] Field of Search .................. 435/190, 191, 435/192, 189, 929, 256.5

[56] References Cited

U.S. PATENT DOCUMENTS 5,370,990  12/1994  Staniford et al. ............... 435/4
5,387,109  2/1995  Ishikawa et al. ................ 435/191

FOREIGN PATENT DOCUMENTS

0364275A2  4/1990  European Pat. Off. .
0526150    2/1993  European Pat. Off. .
0576838A3  1/1994  European Pat. Off. .

OTHER PUBLICATIONS

Horiuchi et al., Agric. Biol. Chem., vol. 55, No. 2, pp. 333–338 (1991).
Horiuchi et al., Agric. Biol. Chem., vol. 53, No. 1, pp. 103–110 (1989).

*Primary Examiner*—Francisco Prats
*Attorney, Agent, or Firm*—Birch, Stewart, Kolasch & Birch, LLP

[57] ABSTRACT

A novel fructosyl amino acid oxidase derived from genus Fusarium or Gibberella, a process for producing the enzyme, an assay of an amadori compound using the enzyme, a reagent or a kit containing the enzyme, a process for producing fructosyl lysine and/or fructosyl $N^\alpha$-Z-lysine as a substrate of a fructosyl amino acid oxidase, which is useful for screening and/or culturing a microorganism capable of producing the enzyme, and a medium containing fructosyl lysine and/or fructosyl $N^\alpha$-Z-lysine for screening and/or culturing a microorganism capable of producing a fructosyl amino acid oxidase is provided.

6 Claims, 15 Drawing Sheets

FRUCTOSYL AMINO ACID OXIDASE AND PROCESS FOR PRODUCING THE SAME

This application is a divisional of application Ser. No. 08/396,761, filed on Mar. 1, 1995, now U.S. Pat. No. 5,789,222, the entire contents of which are hereby incorporated by reference.

FIELD OF THE INVENTION

The present invention relates to a novel fructosyl amino acid oxidase. More particularly, it relates to a novel fructosyl amino acid oxidase derived from genus Fusarium or Gibberella, a process for producing the enzyme, an assay of an amadori compound using the enzyme, and a reagent or a kit containing the enzyme. The present invention also provides a process for producing fructosyl lysine and/or fructosyl $N^\alpha$-Z-lysine as a substrate of a fructosyl amino acid oxidase, which is useful for screening and/or culturing a microorganism capable of producing the enzyme, and a medium containing fructosyl lysine and/or fructosyl $N^\alpha$-Z-lysine for screening and/or culturing a microorganism capable of producing a fructosyl amino acid oxidase.

BACKGROUND OF THE INVENTION

When reactive substances such as protein, peptide and amino acid having an amino group(s) coexist with a reducing sugar such as aldose having an aldehyde group(s), they combine nonenzymatically and irreversibly through the amino and aldehyde groups, which is followed by amadori rearrangement to form an amadori compound. The production rate of an amadori compound being a function of concentration of reactants, period of contact, temperature and the like, various useful information can be derived from the amount of amadori compounds in a sample containing reactive substance(s). Examples of materials containing an amadori compound include food products such as soy sauce and body fluids such as blood.

In a living body, fructosylamines are formed through the reaction between glucose and an amino acid, and the resultant glycated derivatives of hemoglobin, albumin and proteins in blood are called glycohemoglobin, glycoalbumin and fructosamine, respectively. As the concentration of these glycated derivatives in blood reflects an average of blood sugar levels over a particular period of time, it can be a significant index for diagnosis and control of conditions of diabetes. Therefore, the establishment of a method of measuring an amadori compound in blood is clinically useful.

Further, a state of preservation and period after production of a food product can be estimated on the basis of the amount of amadori compounds in the food product. Therefore, the method of measuring an amadori compound can also contribute to the quality control of a food product.

Thus, an assay of amadori compounds should be useful in wide fields involving medicine and food products.

As assay of amadori compounds, there has been known method which utilizes high performance liquid chromatography [Chromatogr. Sci. 10: 659 (1979)], a column filled with solid materials to which boric acid is attached [Clin. Chem. 28: 2088 (1982)], electrophoresis [Clin. Chem. 26:1598 (1980)] or antigen-antibody reaction [JJCLA 18: 620 (1993), J. Clin. Lab. Inst. Reag. 16:33–37 (1993)], a method for measuring the amount of fructosamine [Clin. Chem. Acta 127:87–95 (1982)], a calorimetric determination following the oxidization with thiobarbituric acid [Clin. Chem. Acta 112:179–204 (1981)], or the like. The existing methods, however, require an expensive device(s) and are not necessarily accurate and rapid enough.

In the field of clinical assay and food analysis, a method utilizing enzymatic process has recently been widely used because, owing to characteristics of enzymes (specificity in terms of substrate, reaction, structure, active site, etc.), an intended substance can be selectively analyzed with accuracy and rapidity.

There have already been proposed assays which comprise reacting an oxidoreductase with amadori compounds and determining oxygen consumption or hydrogen peroxide generation as an index of the amount of amadori compounds (e.g. Japanese Patent Publication (KOKOKU) Nos. 5-33997 and 6-65300, and Japanese Laid-Open Patent Publication Nos. 2-195900, 3-155780, 4-4874, 5-192293 and 6-46846). Further, assays of glycated protein for the diagnosis of diabetes have been disclosed (Japanese Laid-Open Patent Publication Nos. 2-195899, 2-195900, 5-192193 and 6-46846).

The decomposition of amadori compounds catalyzed by an oxidoreductase can be represented by the following reaction scheme:

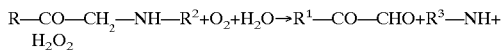

wherein $R^1$ is an aldose residue and $R^2$ is an amino acid, protein or peptide residue.

Examples of enzymes which catalyze the above reaction include fructosyl amino acid oxidase derived from microorganisms [e.g., strains of Corynebacterium (Japanese Patent Publication Nos. 5-33997 and 6-65300), strains of Asperqillus (Japanese Laid-Open Patent Publication No. 3-155780), etc.], ketoamine oxidase derived from microorganisms [e.g., strains of Corynebacterium, Fusarium, Acremonium or Debaryomyces (Japanese Laid-Open Patent Publication No. 5-192193)], fructosylamine deglycase [e.g., strains of Candida (Japanese Laid-Open Patent Publication No. 6-46846)], alkyllysinase which can be prepared according to the method described in J. Biol. Chem., Vol. 239, pp. 3790–3796 (1964), and the like.

Assays involving these existing enzymes, however, had some drawbacks.

For instance, an amadori compound in blood which serves as an index for the diagnosis of diabetes is a glycated protein normally formed when a glucose is bound to a lysine residue at its ∈-position on protein molecule [J. Biol. Chem. 26: 13542–13545 (1986)]. Therefore, it is necessary to use an enzyme highly specific to fructosyl lysine to conduct the determination of glycated proteins efficiently. However, the existing enzyme derived from Corynebacterium does not act on fructosyl lysine. Although an enzyme from Asperqillus acts on fructosyl lysine, it is less reactive with fructosyl lysine compared to other amadori compounds (see Table 5 below). Further, the action on the glycated protein or hydrolysis thereof is still unclear. Although the ketoamine oxidase described in Japanese Laid-Open Patent Publication No. 5-192193 is specific to glycated α-amine group on fructosyl valine, it cannot afford an accurate assay of glycated proteins where a lysine residue is bound to a sugar. Because the fructosylamine deglycase is highly specific to difructosyl lysine, it is not available in an assay specific to a substance having lysine residue which is glycated at the ∈-position.

Furthermore, a method using an alkyllysinase cannot be reliable and accurate because said enzyme lacks in specificity and reacts with substances whose lysine residue is not bonded to only a sugar.

As described above, existing enzymes cannot necessarily give an accurate assay of glycated proteins and therefore the development of an enzyme highly specific to fructosyl lysine has been demanded.

In general, for the improvement of accuracy and usefulness of an assay involving an enzymatic process, it is essential to use an enzyme having a catalytic activity suitable for purposes of the assay. Thus, it is necessary to select an appropriate enzyme taking many factors such as a substance to be determined, as a substrate of the enzyme, the condition of a sample, measuring conditions and the like into consideration in order to carry out the assay with accuracy and reproducibility. To select a suitable enzyme, many enzymes must be previously obtained and characterized regarding the activity, substrate specificity, temperature stability, pH stability and the like. Therefore, it is necessary to develop more and more fructosyl amino acid oxidases and characterize the same.

SUMMARY OF THE INVENTION

The present inventors have intensively studied for purposes of providing a novel fructosyl amino acid oxidase specific to amadori compounds, particularly to glycated protein, and have found that objective enzymes can be obtained by culturing a strain of Fusarium or Gibberella in the presence of fructosyl lysine and/or fructosyl $N^{\alpha}$-Z-lysine.

Thus, the present invention provides a novel fructosyl amino acid oxidase produced by culturing a strain of Fusarium or Gibberella, said strain being capable of producing a fructosyl amino acid oxidase, in a medium containing fructosyl lysine and/or fructosyl $N^{\alpha}$-Z-lysine.

DETAILED DESCRIPTION OF THE INVENTION

The medium containing fructosyl lysine and/or fructosyl $N^{\alpha}$-Z-lysine used for culturing a microorganism capable of producing a fructosyl amino acid oxidase of the present invention comprises fructosyl lysine and/or fructosyl $N^{\alpha}$-Z-lysine (hereinafter, it may be referred to as "FZL") obtained by autoclaving glucose together with lysine and/or FZL at 100 to 150° C. for 3 to 60 minutes. Accordingly, the fructosyl amino acid oxidase of the present invention is an enzyme specific to fructosyl lysine and/or fructosyl $N^{\alpha}$-Z-lysine. Throughout the specification, the term "fructosyl amino acid oxidase" of the present invention is used synonymously with the term "fructosyl lysine oxidase", because it is specific to fructosyl lysine and/or FZL and may hereinafter be referred to as "FLOD".

The enzyme of the present invention can be prepared by culturing a strain of Fusarium or Gibberella capable of producing FLOD in a medium containing fructosyl lysine and/or FZL.

Examples of strains of Fusarium include Fusarium oxysporum S-1F4 (FERM BP-5010).

Examples of strains of Gibberella include *Gibberella fujikuroi* (IFO No. 6356) and *Gibberella fujikuroi* (IFO No. 6605). *Gibberella fujikuroi* G-3802 is a deposit of the strain IFO-6356 that was converted to a deposit under the terms and conditions of the Budapest Treaty by deposit at the National Institute of Bioscience and Human-Technology of the Agency of Industrial Science and Technology, 1–3, Higashi-1-chome Tsukuba-shi, Ibaraki-ken 305, Japan, on Jun. 16, 1997, under the accession number FERM BP-5982.

The present invention also provides a process for producing fructosyl lysine and/or fructosyl $N^{\alpha}$-Z-lysine as a substrate of the enzyme, which is useful for screening and/or culturing a microorganism capable of producing a FLOD.

Further, the present invention provides a medium containing fructosyl lysine and/or fructosyl $N^{\alpha}$-Z-lysine for screening and/or culturing a microorganism capable of producing the said enzyme.

Heretofore, glycated proteins or glycated amino acids have been chemically synthesized according to the method described in Japanese Laid-Open Patent Publication No. 2-69664, which required 8 or more days and complicated procedures.

The present inventors have found that a saccharic amino acid can be produced by autoclaving a monosaccharide and a free or protected amino acid in a solution at 100 to 150° C.

For example, the intended fructosyl lysine and/or FZL can be easily obtained by autoclaving glucose together with lysine and/or $N^{\alpha}$-Z-lysine in a solution. For purposes of the present invention, $N^{\alpha}$-Z-lysine is preferred.

Accordingly, the present invention provides a process for producing a saccharic amino acid, which comprises autoclaving a monosaccharide and a free or protected amino acid in a solution at 100 to 150° C.

The present invention also provides a process for producing fructosyl lysine and/or FZL, which comprises autoclaving 0.01 to 50% (w/w) glucose together with 0.1 to 20% (w/w) lysine and/or $N^{\alpha}$-Z-lysine in a solution at 100 to 150° C. for 3 to 60 minutes.

Thus, the fructosyl lysine and/or FZL can be obtained as a 0.01 to 0.5% aqueous solution of fructosyl lysine and/or FZL produced by autoclaving an aqueous solution containing 0.01 to 50% (w/w) glucose together with 0.01 to 20% (w/w) lysine and/or $N^{\alpha}$-Z-lysine at 100 to 150° C. for 3 to 60 minutes (see, FIG. 1).

Preferably, a solution of a total volume of 1000 ml containing 200 g of glucose and 10 g of $N^{\alpha}$-Z-lysine is prepared and autoclaved at 120° C. for 20 minutes. A purified FZL can be obtained by subjecting the crude aqueous FZL solution obtained according to the method of the present invention to reversed phase chromatography or ion-exchange chromatography.

A medium containing fructosyl lysine and/or FZL can be obtained by adding fructosyl lysine and/or FZL obtained by the method of the present invention described above to any one of conventional media, but it can be conveniently prepared by autoclaving a suitable mixture. For example, a mixture (preferably pH 5.6 to 6.0) comprising 0.01 to 50% (w/w) glucose, 0.01 to 20% (w/w) lysine and/or $N^{\alpha}$-Z-lysine, 0.1% (w/w) $K_2HPO_4$, 0.1% (w/w) $NaH_2PO_4$, 0.05% (w/w) $MgSO_4 \cdot 7H_2O$, 0.01% (w/w) $CaCl_2 \cdot 2H_2O$ and 0.2% (w/w) yeast extract is autoclaved at 100 to 150° C. for 3 to 60 minutes. The resulting medium is novel and is useful for screening and/or culturing a microorganism producing FLOD using fructosyl lysine and/or FZL as a substrate, thereby contributing to the development and research of FLOD. The medium of the present invention is available for screening of any microorganisms capable of growing in said medium. Examples of such a microorganism include strains from a genus of fungus such as Fusarium, Gibberella, Penicillium or Asperqillus, or that from bacterium such as Corynebacterium, but it is not limited to them.

The present invention also provides a medium containing fructosyl lysine and/or FZL as defined above.

As a medium used for the production of FLOD of the present invention, there can be used a normal synthetic or natural medium containing a carbon source, nitrogen source, inorganic substance and other nutrients. As the carbon source, for example, there can be used glucose, xylose, glycerin and the like. As the nitrogen source, for example, there can be used peptone, casein digest, yeast extract, and the like. The inorganic substance can be sodium, potassium, calcium, manganese, magnesium, cobalt, and the like which are usually contained in a normal medium.

The FLOD of the present invention can be induced to the highest extent when a microorganism is cultured in a medium containing fructosyl lysine and/or FZL. Examples of preferred medium include fructosyl lysine- and/or FZL-containing medium (1.0% glucose, 0.5% fructosyl lysine and/or FZL, 1.0% $K_2HPO_4$, 0.1% $NaH_2PO_4$, 0.05% $MgSO_4 \cdot 7H_2O$, 0.01% $CaCl_2 \cdot 2H_2O$ and 0.01% vitamin mixture), in which fructosyl lysine and/or FZL is used as the single nitrogen source and glucose as the carbon source.

A medium (pH 5.6 to 6.0) containing 20 g of glucose, 10 g of fructosyl lysine and/or FZL, 1.0 g of $K_2HPO_4$, 1.0 g of $NaH_2PO_4$, 0.5 g of $MgSO_4 \cdot 7H_2O$, 0.1 g of $CaCl_2 \cdot 2H_2O$ and 2.0 g of yeast extract in 1,000 ml of a total volume is especially preferred.

The medium containing fructosyl lysine and/or FZL can be prepared by adding fructosyl lysine and/or FZL to any of conventional medium, or by autoclaving a medium containing glucose together with lysine and/or $N^\alpha$-Z-lysine. The medium obtainable by either method colored brown owing to the presence of fructosyl lysine and/or FZL and is referred to as "FZL brown-colored medium or GL (glycated lysine and/or glycated $N^\alpha$-Z-lysine) brown-colored medium".

The cultivation is normally conducted at temperature range of 25 to 37° C., preferably 28° C. in a medium of pH range of 4.0 to 8.0, preferably 5.5 to 6.0. However, the culturing conditions may vary depending on various factors such as conditions of microorganisms and should not be limited to those described above.

For example, Fusarium oxysporum S-1F4, when cultured for 20 to 40 hours, preferably 24 hours, under these conditions in a medium, production of FLOD was observed, and when cultured for 24 hours in a preferred medium above, a maximal production of FLOD was observed (see, FIG. 2).

The resultant culture medium is then treated in a conventional manner to remove nucleic acids, cell wall fragments and the like to yield an enzyme preparation.

Since the enzyme activity is normally accumulated in bacterial/fungal cells, cells in the culture are harvested and ground to extract the enzyme.

The grinding of cells can be carried out in a conventional manner, for example, by means of mechanical grinding, autodigestion using a solvent, freezing, ultrasonic treatment, pressurization, or the like.

The method of isolation and purification of an enzyme is also known in the art. It can be conducted by combining known methods such as salting-out with ammonium sulfate, precipitation with an organic solvent such as ethanol, etc., ion-exchange chromatography, gel filtration, affinity chromatography, and the like.

For example, mycelia are harvested by subjecting the resultant culture to centrifugal or suction filtration, washed, suspended in 0.1 M Tris-HCl buffer (pH 8.5), ground with Dino-Mill and centrifuged. The supernatant as cell-free extract is then fractionated with ammonium sulfate and purified by DEAE-Sephacel ion-exchange chromatography.

For purposes of the present invention, FLOD includes any enzyme-containing solutions obtainable throughout the total purification process irrespective of the purity of the enzyme, including the cultured medium as far as the solution has the ability to catalyze the oxidization of amadori compounds.

Further, any fragments of FLOD molecule which are associated to the enzymatic activity of FLOD and maintain the same also fall within the scope of the invention because such fragments are also useful for purposes of the present invention.

The FLOD thus obtained is usable in an assay of amadori compounds, particularly glycated proteins, and is useful for the diagnosis of diabetes.

Accordingly, the present invention provides a process for producing a FLOD, which comprises culturing a strain of fungus in a medium containing a glycated amino acid and/or glycated protein which are optionally protected.

The present invention also provides a process for producing a FLOD, which comprises culturing a strain of Fusarium or Gibberella capable of producing the FLOD in a medium containing fructosyl lysine and/or fructosyl $N^\alpha$-Z-lysine and recovering the FLOD from the resulting culture.

Although all the FLODs produced by strains of both genera are useful to solve the problems to be solved by the present invention, FLODs derived from strains of individual genus are somewhat differ from each other. Accordingly, the FLODs derived from *Fusarium oxysporum* S-1F4 and *Gibberella fujikuroi* are conveniently referred to as FLOD-S and FLOD-G, respectively, as the occasion demands.

Hereinafter, the present invention will be explained in more detail.

(I) FLODs produced by *Fusarium oxysporum* S-1F4

The FLODs of this type have the following physicochemical characteristics:

1) it catalyzes the oxidation of an amadori compound in the presence of oxygen to generate α-ketoaldehyde, amine derivatives and hydrogen peroxide;
2) it is stable in the pH range of about 4.0 to 12.0 with an optimal pH of 8.0;
3) it is stable in the temperature range of about 20 to 55° C. with an optimum temperature of 45° C.; and
4) the molecular weight is about 45,000 (45 kDa) when estimated by gel filtration using Sephacryl S-200 column.

*Fusarium oxysporum* S-1F4 (hereinafter referred to as "S-1F4 strain"), a fungus which produces FLOD of the present invention, is a novel strain which has been isolated from the soil by the present inventors. The mycological characteristics thereof are described below.

The classification of isolated fungus was conducted substantially in accordance with the teaching of "The Genus Fusarium" (CMI. 1971) written by C. Booth.

(1) Growing conditions in medium
  It grows extremely well in each of PDA medium, potato-sucrose agar medium and oatmeal medium. When culturing in a thermostatic chamber at 25° C. for 7 days, strains are spread over a whole petri dish in a felt-like state showing white to light purple color.

(2) Taxonomic properties
  The identification of isolated fungus was carried out through morphological observation as to conidia, conidiophore, etc. under microscopy after cultivating in an oatmeal medium. The observation revealed that a colony of the S-1F4 strain shows white to light purple color, and that a lot of microconidia, macroconidia and thick membrane spores are formed. It was identified as *Fusarium oxysporum* on the basis of the facts that the macroconidia is in a shape of crescent figure and has 3 to 5 of septa and that the microconidia is in a shape of ovoid or ellipse figure and forms pseudocapitate microconidial spores.

This strain S-1F4 had been originally deposited as a domestic microorganism deposit (FERM P-14184, deposition date: Feb. 24, 1994) at the "National Institute of Bioscience and Human-Technology, Agency of Industrial Science and Technology", Tsukuba-shi, Ibaraki-ken, Japan and converted into an international one (FERM BP-5010) under the Budapest Treaty on Feb. 22, 1995.

Characteristics of FLOD-S produced by *Fusarium oxysporum* S-1F4 is described below.

1. Normal induction characteristics

FLOD-S is an inducible enzyme induced by fructosyl lysine and/or fructosyl $N^\alpha$-Z-lysine (FZL) and is produced by culturing *Fusarium oxysporum* S-1F4 strain in a medium containing fructosyl lysine and/or FZL as the nitrogen source and glucose as the carbon source.

The FLOD-S can be induced in a GL brown-colored medium obtained by autoclaving glucose together with lysine and/or $N^\alpha$-Z-lysine but not in a medium containing glucose and lysine and/or $N^\alpha$-Z-lysine which are autoclaved separately, which indicates that the enzyme is specific to amadori compounds.

As to induction effect of substrates, lysine and arginine are fairly effective and lysine is more effective than glycine, demonstrating that the enzyme is more specific to fructosyl lysine as substrate.

2. Reaction specificity and substrate specificity

The FLOD-S has a catalytic activity in the reaction represented by the scheme:

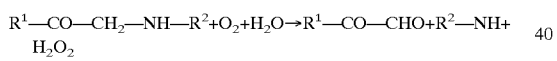

$$R^1-CO-CH_2-NH-R^2+O_2+H_2O \rightarrow R^1-CO-CHO+R^2-NH+ H_2O_2$$

wherein $R^1$ is an aldose residue and R is a protein residue. In the above reaction, amadori compounds of the formula $R^1-CO-CH_2-NH-R^2$ wherein $R^1$ is $-OH$, $-(CH_2)_n-$ or $-[CH(OH)]_n-CH_2OH$ (n is an integer of 0 to 6) and R is $-CHR^3-[CONHR^3]_m COOH$ ($R^3$ is a side chain residue of an α-amino acid and m is an integer of 1 to 480) are preferred as substrate. Among them, compounds wherein $R^3$ is a side chain residue of an amino acid selected from lysine, poly-lysine, valine, asparagine, etc., n is 5 to 6 and m is 55 or less are more preferred.

Both of purified and partially purified FLOD-S were highly specific to FZL. The partially purified enzyme was prepared in the following manner. Thus, S-1F4 strain was grown in a GL brown-colored medium for 24 hours and the culture was filtered with suction to harvest mycelia. The mycelia were then washed, suspended in 0.1 M Tris-HCl buffer (pH 8.5), ground by means of Dino-Mill and centrifuged. The centrifugal supernatant is fractionated with ammonium sulfate and purified using DEAE-Sephacel ion-exchange chromatography to obtain the partially purified enzyme. The purified enzyme was prepared according to the method described in Example 1 below.

The results are shown in Tables 1 and 2.

TABLE 1

Substrate specificity of partially purified FLOD-S derived from S-1F4 strain

| Substrate | Concentration | | Activity (U/ml) | Specific activity (%) |
|---|---|---|---|---|
| Fructosyl $N^\alpha$-Z-lysine | 1.67 | mM | 3.21 | 100 |
| $N^\alpha$-Z-lysine | 1.67 | | N.D.[1] | — |
| L-lysine | 1.67 | | N.D. | — |
| D-glucose | 1.67 | | N.D. | — |
| D-fructose | 1.67 | | N.D. | — |
| Fructosyl poly-L-lysine | 0.018% | | 0.0738 | 2.3 |
| poly-L-lysine | 0.018 | | N.D. | — |
| Fructosyl BSA | 0.83 | | N.D. | — |
| BSA | 0.83 | | N.D. | — |

[1]: not detected

TABLE 2

Substrate specificity of purified FLOD-S derived from S-1F4 strain

| Substrate | Concentration | | Specific activity (%) |
|---|---|---|---|
| Fructosyl $N^\alpha$-Z-lysine | 1.67 | mM | 100 |
| Fructosyl valine | 1.67 | | N.D.[1] |
| $N^\epsilon$-methyl-L-lysine | 1.67 | | N.D. |
| Fructosyl poly-L-lysine | 0.02% | | 2.3 |

[1]: not detected

As is apparent from Tables 1 and 2, FLOD-S of the present invention is remarkably specific to fructosyl $N^\alpha$-Z-lysine (FZL) among substrates tested and is also specific to fructosyl poly-lysine, which demonstrates that the substrate specificity of FLOD-S is quite different from that of known FLODs derived from Corynebacterium or Asperqillus.

3. pH and Temperature conditions

Measurement of pH condition:

FLOD-S was added to the buffer solution (pH 4.0 to 12.0) consisting of 0.1 M acetic acid, potassium phosphate (K—P), Tris-HCl and glycine(Gly)-NaOH buffer. After 10 minutes of incubation at 30° C., the activity was measured under the normal condition (30° C., pH 8.0).

Measurement of temperature condition

To Tris-HCl buffer (pH 8.0) is added FLOD-S at temperature ranging from 25 to 60° C. After 10 minutes of incubation, the activity was evaluated under the normal condition.

When the activity of FLOD-S derived from S-1F4 strain was evaluated according to these methods, said enzyme is stable in the pH range of 4.0 to 12.0, preferably 7.0 to 8.5. The optimum pH is 7.0 to 9.0, preferably 7.5 to 8.5, most preferably 8.0 (see, FIG. 3).

The S-1F4-derived enzyme can be stable at temperature range of 20 to 55° C. The FLOD-S gradually loses the activity at temperature of 30° C. or higher and is completely inactivated at temperature of 60° C. or higher. The enzyme reaction proceeds efficiently at 30 to 50° C., preferably 40 to 50° C., more preferably 45° C. (see, FIG. 4).

4. Evaluation of titer

Titration was carried out as follows:

(1) Method utilizing calorimetric determination of generated hydrogen peroxide

A. Measurement of generation rate

A 50 mM FZL solution was prepared by dissolving FZL previously obtained in distilled water. To a mixture of 100 μl of 45 mM 4-aminoantipyrine, 100 μl of peroxidase (60 U/ml), 100 μl of 60 mM phenol, 1 ml of 0.1 M Tris-HCl buffer (pH 8.0) and 50 μl of enzyme solution was added distilled water to give a total volume of 2.9 ml and the solution was allowed to equilibrate at 30° C. After the addition of 100 μl of 50 mM FZl solution, the time-course of absorbance at 505 nm was measured. The amount (μmol) of hydrogen peroxide produced in one minute was calculated on the basis of a molar absorption coefficient ($5.16 \times 10^3$ $M^{-1}cm^{-1}$) of a quinone pigment produced. The resultant numerical value was taken as a unit(U) of enzyme activity.

B. End point method

According to the same manner as that described in the above method A, a solution was prepared and a substrate solution was added thereto. After 30 minutes of incubation at 30° C., absorbance at 505 nm was measured. The enzyme activity was evaluated on the basis of the amount of hydrogen peroxide produced referring to a calibration curve previously obtained using a standard hydrogen peroxide solution.

(2) Method of determination of oxygen absorption due to enzyme reaction

After 1 ml of 0.1 M Tris-HCl buffer (pH 8.0) was mixed with 50 μl of an enzyme solution, distilled water was added to obtain a total volume of 2.9 ml and the resulting solution was charged in a cell of an oxygen electrode manufactured by Lank Brothers Co. The solution was stirred at 30° C. to allow the dissolved oxygen to be equilibrated under the temperature and 100 μl of 50 mM FZL was added to it. Then, the oxygen absorption was continuously measured on a recorder to obtain an initial rate. The amount of oxygen absorbed in one minute was determined on the basis of a calibration curve, which was taken as an enzyme unit.

5. Inhibition, activation and stabilization of enzyme (1) Effect of metal

To an enzyme solution was added a solution containing metal to be tested at a final concentration of 1 mM under the condition of 0.1 M Tris-HCl buffer (pH 8.0). After 5 minutes of incubation at 30° C., the enzyme activity was evaluated. The results are shown in Table 3 below.

TABLE 3

Effect of metal ion on the activity of FLOD-S derived from S-1F4 strain

| Metal (1 mM) | Specific activity (%) | Metal (1 mM) | Specific activity (%) |
| --- | --- | --- | --- |
| None | 100 | $FeSO_4$ | 97 |
| LiCl | 100 | $CoSO_4$ | 42 |
| KCl | 104 | $CuCl_2$ | 0 |
| NaCl | 107 | $ZnSO_4$ | 0 |
| RbCl | 103 | $AgNO_3$ | 0 |
| $CsCl_2$ | 102 | $BaCl_2$ | 60 |
| $MgCl_2$ | 75 | $HgCl_2$ | 0 |
| $CaCl_2$ | 77 | $FeCl_3$ | 67 |
| $MnCl_2$ | 154 | | |

As is apparent from Table 3, the activity of FLOD-S is slightly inhibited by a divalent metal ion and is completely inhibited by $Ag^+$, $Hg^+$, $Cu^{2+}$ and $Zn^{2+}$.

(2) Effect of various inhibitors

The inhibitory effect (2) Effect of various inhibitors tested in a manner substantially analogous to that described in (1) above. In the present test, the final concentration of PCMB (parachloro mercuric benzoate) is 0.1 mM while that of others 1 mM. The results are shown in Table 4. The stabilization effect was examined by dialyzing the mixture overnight against 50 mM Tris-HCl buffer (pH 8.5) containing 2 mM dithiothreitol (DTT) and measuring the enzyme activity.

TABLE 4

Effect of various inhibitors on activity of FLOD-S derived from S-1F4 strain

| Reagent (1 mM) | Specific activity (%) |
| --- | --- |
| None | 100 |
| PCMB* | 0 |
| 5,5',-Dithiobis(2-nitrobenzoic acid) | 95 |
| Iodoacetic acid | 102 |
| Sodium azide | 101 |
| α,α'-Dipyridyl | 106 |
| O-Phenanthrolene | 103 |
| Semicarbazide | 103 |
| Phenylhydrazine | 2.6 |
| Hydrazine | 13 |
| Hydroxylamine | 21 |
| Clorgyline | 132 |
| Deprenyl | 102 |
| Aminoguanidine | 66 |

*: 0.1 mM

As is apparent from Table 4, the activity of FLOD-S is completely inhibited by PCMB. Further, it is also inhibited by phenylhydrazine or hydrazine. These results indicate that a SH group and/or a carbonyl group may play an important role in the expression of enzyme activity.

The enzyme is stabilized by dithiothreitol (DTT), and preferable solvent for the preservation is 50 mM Tris-HCl buffer (pH 8.5) containing 2 mM DTT.

6. Molecular weight

Molecular weight was estimated by column gel filtration on Sephacryl S-200 and by SDS-PAGE (sodium dodecylsulfate polyacrylamide gel electrophoresis). The column chromatography was conducted using 0.1 M Tris-HCl buffer (pH 8.5) containing 0.1 M NaCl, and molecular weight was estimated using several standards of known proteins, which were treated in the same manner, on the basis of the elution volume.

SDS-PAGE was conducted according to the Davis's method (40 mA, 3 hours, and 10% gel). Protein was stained with Coumassie brilliant blue G-250. Molecular weight was estimated using several standards of known proteins such as phosphorylase B, bovine serum albumin, ovalbumin, carbonic anhydrase and soybean trypsin inhibitor, which were treated in the same manner, using a calibration curve.

As a result, the molecular weight of FLOD-S derived from S-1F4 strain was about 45,000(45 kDa) on column gel filtration using Sephacryl S-200, and about 50,000 (50 kDa) on SDS-PAGE (see, FIGS. 5 and 6).

7. Isoelectric point

Isoelectric point (pI), when measured by disc electrofocusing method, was 4.8 for FLOD-S derived from S-1F4 strain.

8. Comparison with known enzymes

FLOD-S derived from S-1F4 strain of the present invention was compared with known fructosyl amino acid oxidases derived from various microorganisms.

TABLE 5

Comparison of various fructosyl amino acid oxidases derived from microorganisms

|  | Fusarium oxysporum S-1F4 | Corynebacterium sp.[1] | Aspergillus sp.[2] |
|---|---|---|---|
| Molecular weight (gel filtration) | 45,000 | 88,000 | 83,000 |
| Molecular weight (SDS-PAGE) | 50,000 | 44,000 | 43,000 |
| Coenzyme | Covalently-bound FAD | Noncovalently-bonded FAD | Noncovalently-bonded FAD |
| Fructosyl lysine specificity | 45.9[3] | N.D.[4] | 11.28[4] |
| Fructosyl valine specificity (U/mg protein) | N.D. | 7.09 | 59.8 |
| Michaelis constant | 0.22 mM (for Fructosyl lysine) | 0.74 mM (for Fructosyl glycine) | 2.2 mM (for Fructosyl glycine) |
| Optimum pH | 8.0 | 8.3 | 7.7 |
| Inactivation by SH reagent | inactivated | not inactivated | inactivated |
| Optimum temperature (° C.) | 45 | 40 | 40 |
| Isoelectric point | 4.8 | 4.6 | 6.8 |

1): T. Horiuchi et al., Agric. Biol. Chem., 53 (1), 103–110 (1989)
2): T. Horiuchi et al., Agric. Biol. Chem., 55 (2), 333–338 (1991)
3): Specific activity to fructosyl-$N^\alpha$-Z-lysine
4): Specific activity to N-o-fructosyl $N^\alpha$-formyllysine As is apparent from Table 5, the following differences can be observed between FLOD-S of the present invention and others derived from two strains.

(1) Molecular weight: in fungal cells, FLOD-S of the present invention is produced as a monomer while other two enzymes as a dimer.

(2) Coenzyme: coenzyme for FLOD-S of the present invention is covalently-bonded FAD, while that for other enzymes is noncovalently-bonded FAD.

(3) Substrate specificity: difference in specificity to fructosyl lysine as a substrate is observed. That is, FLOD-S of the present invention is highly specific to fructosyl lysine, while the enzyme derived from Corynebacterium does not act on fructosyl lysine, and the one derived from Asperqillus acts on fructosyl lysine only to a lesser extent compared to fructosyl valine.

(4) Michaelis constant: the difference in Michaelis constant indicates that an affinity of FLOD-S to the substrate FZL is higher than that of other enzymes.

(5) Optimum pH, optimum temperature, isoelectric point and inhibition by SH reagents: the data indicate that FLOD-S of the present invention is distinguishable from other enzymes.

(II) FLODs produced by Gibberella

The FLODs of this type have the following physico-chemical characteristics:

1) it catalyzes the oxidation of an amadori compound in the presence of oxygen to generate α-ketoaldehyde, amine derivatives and hydrogen peroxide;
2) an optimum pH is 8.0;
3) it is stable in the temperature range of 20 to 50° C. with an optimum temperature of 35° C.; and
4) the molecular weight is about 47,000 (47 kDa) when estimated by gel filtration using Superdex 200 pg.

Characteristics of FLOD-G produced by Gibberella is described below.

1. Normal induction characteristics

FLOD-G is an inducible enzyme induced by fructosyl lysine and/or fructosyl $N^\alpha$-Z-lysine (FZL) and is produced by culturing a FLOD-producing strain of Gibberella in a medium containing fructosyl lysine and/or FZL as the nitrogen source and glucose as the carbon source.

The FLOD-G can be induced in a GL brown-colored medium obtained by autoclaving glucose together with lysine and/or $N^\alpha$-Z-lysine but not in a medium containing glucose and lysine and/or $N^\alpha$-Z-lysine, which are autoclaved separately, indicating that the enzyme is specific to amadori compounds.

2. Reaction specificity and substrate specificity

The FLOD-G has a catalytic activity in the reaction represented by the scheme:

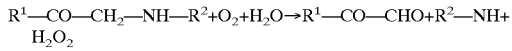

$$R^1\text{—CO—CH}_2\text{—NH—}R^2 + O_2 + H_2O \rightarrow R^1\text{—CO—CHO} + R^2\text{—NH} + H_2O_2$$

wherein $R^1$ is an aldose residue and $R^2$ is a protein residue. In the above reaction, amadori compounds of the formula $R^1\text{—CO—CH}_2\text{—NH—}R^2$ wherein $R^1$ is —OH, —(CH$_2$)$_n$— or —[CH(OH)]$_2$—CH$_2$OH (n is an integer of 0 to 6) and $R^2$ is —CHR$^3$—[CONHR$^3$]$_m$COOH (R$^3$ is a side chain residue of an α-amino acid and m is an integer of 1 to 480) are preferred as substrate. Among them, compounds wherein $R^3$ is a side chain residue of an amino acid selected from lysine, poly-lysine, valine, asparagine, etc., n is 5 to 6 and m is 55 or less are more preferred. The FLOD-G is highly specific to FZL as shown in Table 6 below.

TABLE 6

Substrate specificity of FLOD-G derived from *Gibberella fujikuroi*

| Substrate | Concentration | | Specific activity (%) |
|---|---|---|---|
| $N^\epsilon$-Fructosyl $N^\alpha$-Z-lysine | 1.67 | mM | 100 |
| Fructosyl valine | 1.67 | | N.D.[1] |
| $N^\epsilon$-Methyl-L-lysine | 1.67 | | N.D. |
| Fructosyl poly-L-lysine | 0.017% | | 1.0 |
| Poly-L-lysine | 0.017 | | N.D. |
| FBSA[2] | 0.17 | | N.D. |
| FHSA[3] | 0.17 | | N.D. |
| Tryptic FBSA | 0.17 | | 0.19 |
| Tryptic FHSA | 0.17 | | N.D. |
| Tryptic fructosyl poly-L-lysine | 0.17 | | 59.7 |

1): not detected
2): fructosyl bovine serum albumin
3): fructosyl human serum albumin As is apparent from Table 6, FLOD-G of the present invention is active on fructosyl poly-lysine and is active on protease digest of glycated protein.

3. pH and Temperature conditions

An optimum pH, when measured in a manner similar to that described in (I), 3 above, is 8.0 (see, FIG. 7).

Activity of FLOD-G was measured under a conventional condition at temperature ranging from 20 to 60° C. after 10 minutes of incubation in Tris-HCl buffer (pH 8.0).

When the activity of FLOD-G was evaluated according to the method above, said enzyme is stable at temperature ranging from 20 to 50° C., preferably 20 to 40° C., more preferably 20° C. The enzyme reaction proceeds efficiently at temperature ranging from 20 to 50° C., preferably 20 to 40° C., more preferably 35° C. (see, FIG. 8).

4. Evaluation of titer

Titration was carried out as follows:

(1) Method utilizing calorimetric determination of generated hydrogen peroxide

A. Measurement of generation rate

A 100 mM FZL solution was prepared by dissolving FZL previously obtained in distilled water. To a mixture of 100 μl of 45 mM 4-aminoantipyrine, 100 μl of peroxidase solution (60 U/ml), 100 μl of 60 mM phenol, 1 ml of 0.1 M Tris-HCl buffer (pH 8.0) and 50 μl of enzyme solution, was added distilled water to give a total volume of 2.95 ml and the solution was allowed to be equilibrated at 30° C. After the addition of 50 μl of 100 mM FZL solution, the time-course of absorbance at 505 nm was measured. The amount (μmol) of hydrogen peroxide produced in one minute was calculated on the basis of a molar absorption coefficient ($5.16 \times 10^3$ $M^{-1}cm^{-1}$) of a quinone pigment produced. The resultant numerical value was taken as a unit (U) of enzyme activity.

B. End point method

According to the same manner as that described in the above method A, a solution was prepared and a substrate solution was added thereto. After 30 minutes of incubation at 30° C., absorbance at 505 nm was measured. The enzyme activity was evaluated on the basis of the amount of hydrogen peroxide produced using a calibration curve previously obtained using a standard hydrogen peroxide solution.

(2) Method of determination of oxygen absorption due to enzyme reaction

After 1 ml of 0.1 M Tris-HCl buffer (pH 8.0) was mixed with 50 μl of an enzyme solution, distilled water was added to obtain a total volume of 3.0 ml and the resulting solution was charged in a cell of an oxygen electrode manufactured by Lank Brothers Co. The solution was stirred under 30° C. to allow the dissolved oxygen to be equilibrated under the temperature and 100 μl of 50 mM FZL was added. Then, the oxygen absorption was continuously measured on a recorder to obtain an initial rate. The amount of oxygen absorbed in one minute was determined on the basis of a calibration curve, which was taken as an enzyme unit.

6. Inhibition, activation and stabilization of enzyme (1) Effect of metal

To an enzyme solution was added a solution of a metal to be tested at a final concentration of 1 mM under the condition of 0.1 M Tris-HCl buffer (pH 8.0) and pre-incubated for 5 minutes at 30° C. Then, the enzyme activity was evaluated. The results are shown in Table 7 below.

TABLE 7

Effect of metal ion on the activity of FLOD-G derived from *Gibberella fujikuroi* (IFO No. 6605)

| Metal (1 mM) | Specific activity (%) | metal (1 mM) | specific activity (%) |
|---|---|---|---|
| None | 100 | $FeSO_4$ | 74 |
| LiCl | 96 | $CoSO_4$ | 15 |
| KCl | 98 | $CuCl_2$ | 2 |
| NaCl | 97 | $ZnSO_4$ | 33 |
| RbCl | 97 | $AgNO_3$ | 0 |
| $CsCl_2$ | 97 | $BaCl_2$ | 103 |
| $MgCl_2$ | 94 | $HgCl_2$ | 25 |
| $CaCl_2$ | 97 | $FeCl_3$ | 16 |
| $MnCl_2$ | 115 | | |

As is apparent from Table 7, the activity of FLOD-G is inhibited by $Co^{2+}$, $Cu^{2+}$, $Zn^{2+}$, $Hg^{2+}$ and $Fe^{3+}$, and is completely inhibited by $Ag^+$.

(2) Effect of various inhibitors

The inhibitory effect of various substances was tested in a manner substantially analogous to that described in (1) above. The results are shown in Table 8. The stabilization effect was examined by dialyzing overnight against 50 mM Tris-HCl buffer (pH 8.5) containing 2 mM DTT and measuring the activity.

TABLE 8

Effect of various inhibitors on the activity of FLOD-G derived from *Gibberella fujikuroi*

| Inhibitor (mM) | Specific activity (%) | Inhibitor (mM) | Specific activity (%) |
|---|---|---|---|
| None | 100 | semicarbazide | 77 |
| PCMB[1]' | 51 | phenylhydrazine | 13 |
| DTNB[2] | 76 | hydrazine | 14 |
| Iodoacetic acid | 77 | hydroxylamine | 16 |
| Sodium azide | 78 | Deprenyl | 81 |
| α,α'-Dipyridyl | 78 | aminoguanidine | 50 |
| O-phenanthrolene | 78 | EDTA | 81 |

1): Parachloro mercuric benzoate
2): 5,5'-Dithiobis(2-nitrobenzoic acid)
3): 0.1 mM As is apparent from Table 8, the activity of FLOD-G is strongly inhibited by PCMB, hydrazine, phenylhydrazine, hydroxylamine and aminoguanidine, indicating that a SH group and/or a carbonyl group may play an important role in the expression of enzyme activity.

The enzyme is stabilized by dithiothreitol, and preferable solvent for the preservation is 50 mM Tris-HCl buffer (pH 8.5) containing 2 mM dithiothreitol.

6. Molecular weight

The molecular weight was about 47,000 (47 kDa) when estimated by gel filtration on Superdex 200 pg (see, FIG. 9), and 52,000 (52 kDa) when estimated by SDS-PAGE using several standards of known proteins such as phosphorylase B, bovine serum albumin, ovalbumin, carbonic anhydrase and soybean trypsin inhibitor (see, FIG. 10). These results mean that the FLOD-G is a monomer. SDS-PAGE was conducted in a manner similar to that described in (I), 6 above.

7. Comparison with known enzymes

FLOD-G of the present invention was compared with known fructosyl amino acid oxidases derived from various microorganisms. The results are shown in Table 9 below.

TABLE 9

Comparison of various fructosyl amino acid oxidases derived from microorganisms

| Strain | *Gibberella fujikuroi* | Corynebacterium sp.[1] | Aspergillus sp.[2] |
|---|---|---|---|
| Molecular weight | | | |
| (gel filtration) | 47,000 | 88,000 | 83,000 |
| (SDS-PAGE) | 52,000 | 44,000 | 43,000 |
| Coenzyme | covalently-bonded FAD | noncovalently-bonded FAD | noncovalently-bonded FAD |
| Substrate specificity | | | |
| (U/mg·protein) | | | |
| (Fructosyl lysine) | 48.3[3] | N.D.[4] | 11.28[4] |
| (Fructosyl valine) | N.D. | 7.09 | 59.8 |
| Michaelis constant | 0.13 mM | 0.74 mM | 2.2 mM |
| | for FZL | for fructosyl glycine | for fructosyl glycine |
| Optimum pH | 8.0 | 8.3 | 7.7 |
| Optimum temperature (° C.) | 35 | 40 | 40 |
| Inactivation by SH reagent | inactivated | not inactivated | inactivated |

[1]: Horiuchi et al., Agric. Biol. Chem., 53 (1), 103–110, 1989
[2]: Horiuchi et al., Agric. Biol. Chem., 55 (2), 333–338, 1991
[3]: Specific activity for FZL
[4]: Specific activity for N-o-fructosyl $N^\alpha$-formyllysine As is apparent from Table 9, the following differences can be observed between FLOD-G of the present invention and others derived from two strains.

(1) Molecular weight: in fungal cells, FLOD-G of the present invention is produced as a monomer while other two enzymes as a dimer.

(2) Coenzyme: coenzyme for FLOD-G of the present invention is covalently-bonded FAD, while that for other enzymes is noncovalently-bonded FAD.

(3) Substrate specificity: FLOD-G of the present invention is highly specific to fructosyl lysine without effecting on fructosyl valine, while the enzyme derived from Corynebacterium does not act on fructosyl lysine, and the one derived from Asperqillus acts on fructosyl lysine only to a lesser extent compared to fructosyl valine.

(4) Michaelis constant: the difference in Michaelis constant indicates that an affinity of FLOD-G to the substrate FZL is higher than that of other enzymes.

(5) Optimum pH, optimum temperature and inhibition by SH reagents: the results revealed that FLOD-G of the present invention is distinguishable from other enzymes.

As described above, the enzyme FLODs produced by strains of Fusarium or Gibberella according to the method of the present invention are useful in an assay of amadori compounds.

Accordingly, the present invention provides an assay of an amadori compound in a sample, which comprises bringing the sample containing the amadori compound into contact with FLOD of the present invention and determining the amount of oxygen consumed or that of hydrogen peroxide produced. The assay of the present invention is based on the measurement of the amount of glycated protein and/or glycation rate or the determination of fructosamine in a sample derived from a living body.

The enzyme activity of FLOD is evaluated by the following reaction scheme:

$$R^1-CO-CH_2-NH-R^2+O_2 \rightarrow R^1-CO-CHO+R^2-NH+H_2O_2$$

wherein $R^1$ is an aldose residue and $R^2$ is an amino acid, protein or peptide residue.

As a sample solution to be tested, there can be used any solutions containing an amadori compound(s), for example, those derived from food products such as soy sauce, etc. and from a living body such as blood (e.g. whole blood, plasma or serum), urine, or the like.

The FLOD of the present invention is reacted with a sample containing an amadori compound in a suitable buffer. The suitable pH and temperature of the reaction mixture may vary depending on the enzyme to be used and the sample to be tested. For example, in the case of FLOD-S, it is preferred that the pH of the reaction solution is 4.0 to 12.0, preferably 8.0 and the temperature 20 to 55° C., preferably 30 to 45° C., more preferably 45° C.

In the case of FLOD-G, it is preferred that the pH of the reaction solution is 4.0 to 12.0, preferably 8.0 and the temperature is 20 to 50° C., preferably 35° C.

Tris-HCl buffer can be used as a buffer.

The amount of FLOD to be used in an assay is normally 0.1 unit/ml or more, preferably 1 to 100 units/ml in the case of end point method.

For purposes of the present invention, the determination of amadori compounds can be carried out by any one of known assays shown below.

(1) Determination based on the amount of hydrogen peroxide generated

The amount of amadori compounds in a sample can be estimated from the amount of hydrogen peroxide produced using any methods for determination of hydrogen peroxide. Thus, the hydrogen peroxide can be measured by a colorimetric method, a method utilizing a hydrogen peroxide electrode, etc. The amount of amadori compound in a sample is then estimated using a calibration curve concerning the relation between the amount of hydrogen peroxide and that of amadori compounds. Specifically, the estimation can be conducted in a manner similar to that described in (I), 4 or (II), 4 above, except that the amount of FLOD is 1 unit/ml and that a sample to be added is diluted before the measurement of hydrogen peroxide produced.

As the color-developing system for hydrogen peroxide, there can be used any one of combinations of 4-aminoantipyrine/N-ethyl-N-(2-hydroxy-3-sulfopropyl)-m-toluidine, 4-aminoantipyrine/N,N-dimethylaniline, 4-aminoantipyrine/N,N-diethylaniline, MBTH/N,N-dimethylaniline, 4-aminoantipyrine/2,4-dichlorophenol, etc. in place of 4-aminoantipyrine/phenol.

(2) Determination on the basis of the amount of oxygen consumed

Amadori compound in a sample can be estimated from the amount of oxygen consumed which is calculated by subtracting the amount of oxygen at the completion of reaction from the one at the beginning of reaction using a calibration curve concerning the relation of the amount of oxygen consumed and that of amadori compounds. Specifically, it can be conducted in a manner similar to the titration described in (I), 4, or (II), 4 above, except that the amount of FLOD is 1 unit/ml and that a sample to be added is previously diluted appropriately before the measurement of oxygen consumed.

According to the assay of the present invention, a sample solution can be used as it is, but it may be preferred in a certain occasion that the sample is pre-treated so as to liberate lysine residue to which sugar is bound from glycated protein.

For such a purpose, the sample is treated with a protease (enzymic method) or a chemical substance such as hydrochloric acid, etc. (chemical method). The enzymic method is preferred. Proteases usable in the process of the present invention are known to one of skilled in the art, for example, trypsin, carboxypeptidase B, papain, aminopeptidase, chymotrypsin, thermolysine, subtilisin, proteinase K, pronase and the like. The method of the enzyme treatment is also known and, for example, the trypsin treatment can be conducted as described in Examples below.

As described above, FLOD of the present invention is highly specific to fructosyl lysine contained in glycated proteins, and thereby being useful for the diagnosis and control of conditions of diabetes through the determination of glycated proteins in blood sample. When blood (e.g. whole blood, plasma or serum) is to be assayed, a blood sample derived from a living body can be used as it is or after pre-treatment such as dialysis, etc.

Further, enzymes (e.g. FLOD, peroxidase, etc.) used in the process of the present invention can be used in a liquid state or after immobilizing to suitable solid supports. When enzyme is immobilized to beads and filled into a column which is then attached to an automated device, a routine assay such as clinical examination where a lot of specimens must be tested can be facilitated. The immobilized enzyme has another advantage in view of economical efficiency because it can be used repeatedly.

Furthermore, it is possible to provide a kit by combining an enzyme(s) with a color-developing reagent(s) in an appropriate manner. Such a kit is useful for both of clinical assay and food analysis of amadori compounds.

The immobilization of the enzyme can be conducted by a method known in the art. For example, it is conducted by a carrier bonding method, cross-linkage method, inclusion method, complexing method, and the like. Examples of carriers include polymer gel, microcapsule, agarose, alginic acid, carrageenan, and the like. The enzyme can be bound to a carrier through covalent bond, ionic bond, physical absorption, biochemical affinity, etc. according to a method known in the art.

When using the immobilized enzyme, the assay may be carried out in flow or batch system. As described above, the immobilized enzyme is particularly useful for a routine assay (clinical examination) of glycated proteins in blood samples. When the clinical examination is directed to the diagnosis of diabetes, the result as criterion for diagnosis of diabetes is expressed in fructosamine value or concentration of glycated protein or glycation rate, i.e., the ratio of the concentration of glycated protein to that of whole protein in the sample. The whole protein concentration can be determined in a conventional manner, for example, through the measurement of absorbance at 280 nm or natural fluorescence of albumin, or by Lowry method.

The present invention also provides a reagent or a kit used in an assay of amadori compounds, which comprises FLOD of the present invention and a buffer whose pH is preferably 7.5 to 8.5, more preferably 8.0. When FLOD is immobilized, the solid support can be selected from a polymer gel and the like, and alginic acid is preferred.

In the case of end point assay, the reagent usually contains 1 to 100 units/ml of FLOD for a sample, and Tris-HCl buffer (pH 8.0) as a buffer.

When amadori compounds are assayed on the basis of generated hydrogen peroxide, as the color-developing system, a combination selected from a group consisting of 4-aminoantipyrine/N-ethyl-N-(2-hydroxy-3-sulfopropyl)-m-toluidine, 4-aminoantipyrine/N,N-dimethylaniline, 4-aminoantipyrine/N,N-diethylaniline, MBTH/N,N-dimethylaniline, 4-aminoantipyrine/2,4-dichlorophenol, etc. can be used in place of 4-aminoantipyrine/phenol.

The reagent used in an assay of amadori compound of the present invention may be combined with a suitable color-developing agent together with a color criterion or a standard substance to give a kit which is useful for a preliminary diagnosis or examination.

The reagent or the kit described above is used for measurement of the amount of glycated protein and/or glycation rate or the determination of fructosamine in a sample derived from a living body.

As is apparent from the description above, FLOD of the present invention differs from existing analogous fructosyl amino acid oxidases in substrate specificity and the like, and is specific to fructosyl lysine and therefore is useful in the development of novel clinical assays and food analyses. As a result, it can greatly contribute to the diagnosis of diabetes and quality control of food products. In particular, it is useful in a diagnosis of diabetes where the amount of glycated protein and/or glycation rate in blood is used as an index for diagnosis or control of conditions of diabetes. It is now possible to determine glycated proteins accurately and efficiently by means of assay using a reagent of the present invention for determination of amadori compounds, which facilitates the diagnosis or control of conditions of diabetes.

Fructosyl lysine and/or FZL of the present invention which is useful for screening and/or culturing a microorganism capable of producing FLOD can be prepared efficiently by the method of the present invention. The GL-brown colored medium containing the fructosyl lysine and/or FZL is useful for effecting an efficient cultivation of a microorganism capable of producing FLOD.

Figure 1:
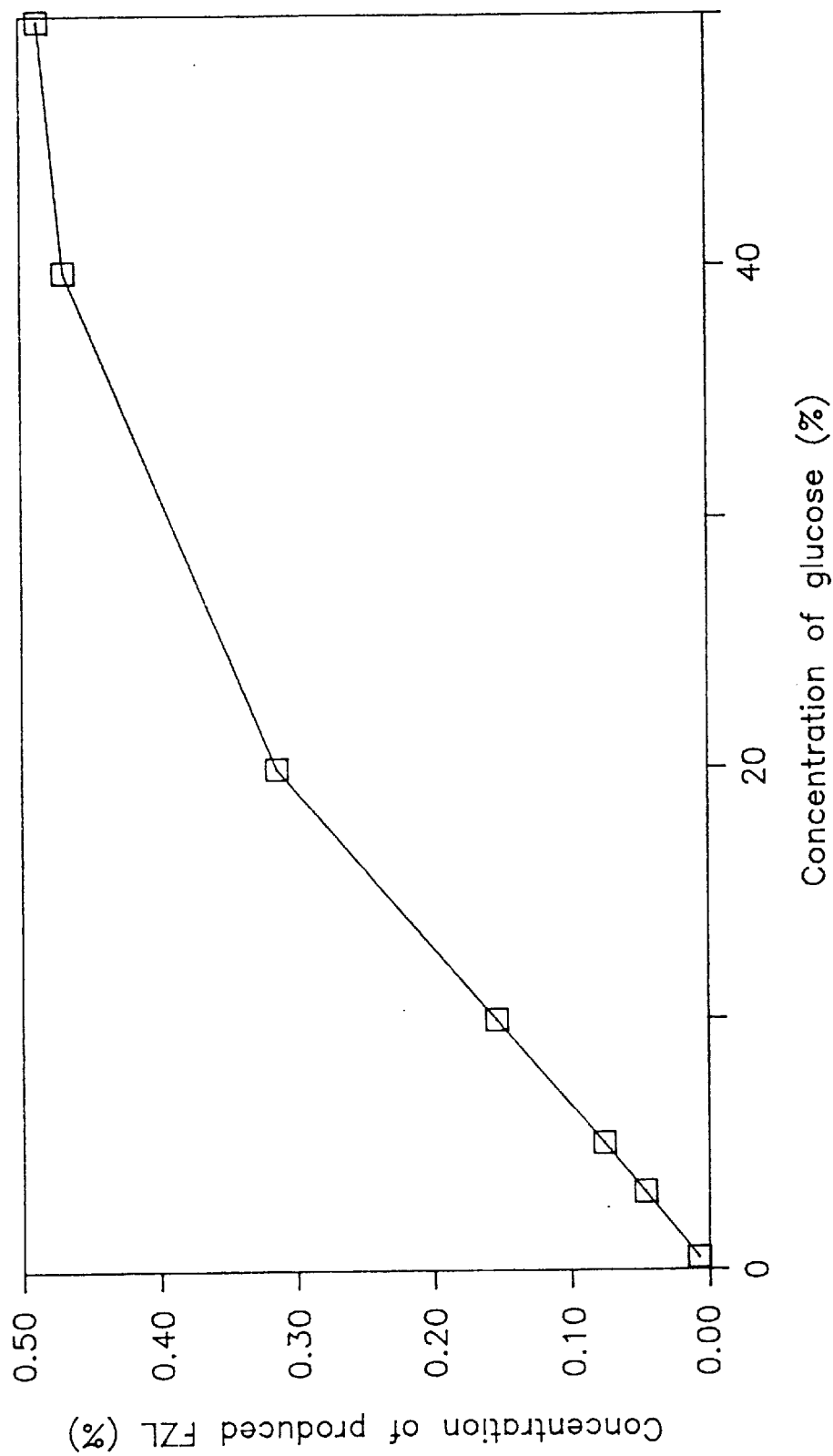
FIG. 1 is a graph illustrating a relation between the concentration of glucose and the amount of fructosyl $N^\alpha$-Z-lysine produced by autoclaving glucose together with 1% $N^\alpha$-Z-lysine.
Figure 2:
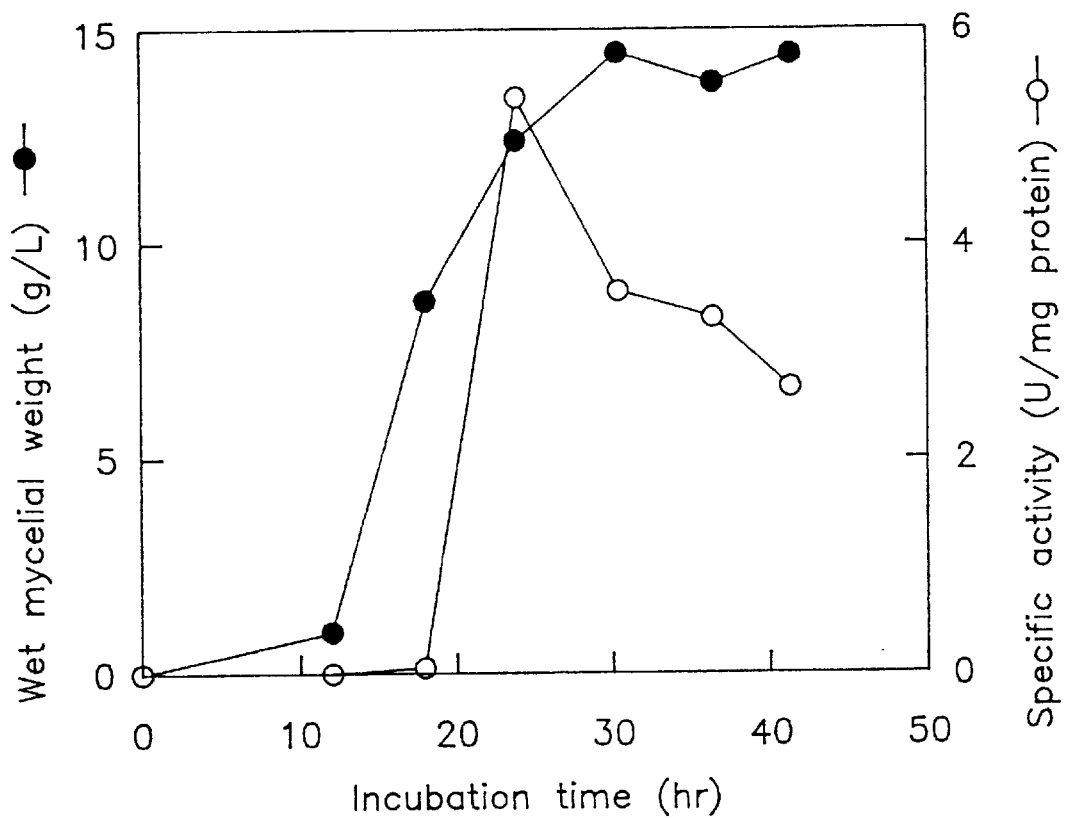
FIG. 2 is a graph illustrating a relation between the cultivation time and the amount of FLOD produced in a culture medium.
Figure 3:
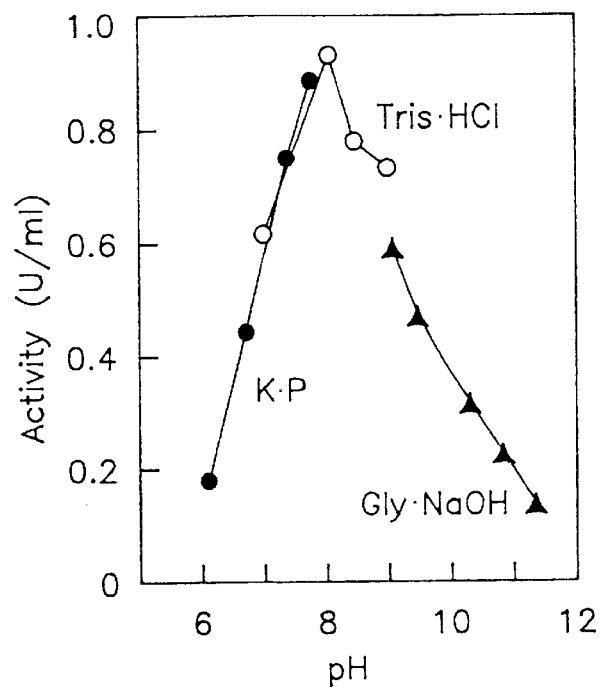
FIG. 3 is a graph illustrating a relation between the pH and the activity of FLOD-S derived from S-1F4 strain in a solvent.
Figure 4:
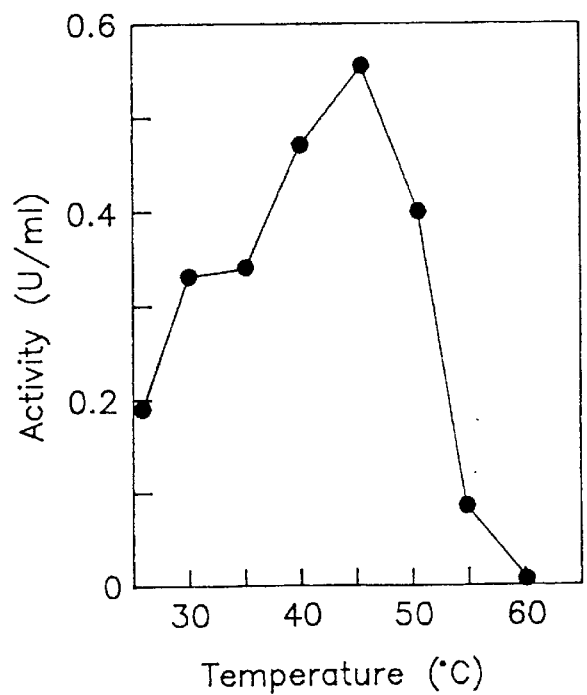
FIG. 4 is a graph illustrating a relation between the temperature and the activity of FLOD-S derived from S-1F4 strain in a solvent.

The following Examples further illustrate the present invention in detail but are not to be construed to limit the scope thereof.

EXAMPLE 1

Preparation and Purification of FLOD-S Derived from Fusarium oxysporum S-1F4

Fusarium oxysporum S-1F4 (FERM BP-5010) was inoculated into a medium (pH 6.0, 10 L) containing 0.5% FZL, 1.0% glucose, 0.1% dipotassium phosphate, 0.1% monosodium phosphate, 0.05% magnesium sulfate, 0.01% calcium chloride and 0.2% yeast extract, and grown at 28° C. for 24 hours with aeration (2 L/min) and stirring (400 rpm) using a jar fermentor. The culture was filtered to harvest mycelia. A portion of mycelia (200 g) was suspended in 0.1 M Tris-HCl buffer (pH 8.5, 1 L) containing 2 mM DTT and ground with Dino-Mill. The ground mixture was centrifuged at 10,000 rpm for 15 minutes to give a crude enzyme solution (cell-free extract). To the crude enzyme solution was added ammonium sulfate to 40% saturation and the mixture was stirred and centrifuged at 12,000 rpm for 10 minutes. To the supernatant was added ammonium sulfate to 75% saturation and the mixture was stirred and centrifuged at 12,000 rpm for 10 minutes. The precipitates were dissolved in 50 mM Tris-HCl buffer (pH 8.5) containing 2 mM DTT (hereinafter, referred to as "buffer A") and the solution was dialyzed overnight against the buffer A. The dialyzed substance was adsorbed onto DEAE-Sephacel column equilibrated with the buffer A. After washing with the buffer A, the column was eluted with a linear gradient of 0 to 0.5 M potassium chloride. The active fractions were collected and fractionated with ammonium sulfate ranging from 55 to 75%, followed by overnight dialysis against the buffer A. To the dialyzed substance was added ammonium sulfate to 25% saturation, which substance was then adsorbed onto a phenyl-Toyopearl column equilibrated with the buffer A containing 25% ammonium sulfate. After washing with the same buffer, the column was eluted with a linear gradient of 25 to 0% saturation of ammonium sulfate. The active fractions were collected. After addition of ammonium sulfate to 40% saturation, the solution was adsorbed onto a butyl-Toyopearl column equilibrated with the buffer A containing 40% saturated ammonium sulfate. After washing with the same buffer, the column was eluted with a linear gradient of 40 to 0% saturation of ammonium sulfate. The active fractions were collected. To the solution was added ammonium sulfate to 80% saturation. The mixture was stirred and centrifuged at 12,000 rpm for 10 minutes. The precipitates were dissolved in 0.1 M buffer A to give an enzyme solution. The enzyme solution was subjected to gel filtration chromatography using Sephacryl S-200 equilibrated with buffer A containing 0.1 M potassium chloride. The active fractions were collected and concentrated by means of ultrafiltration. The concentrate, when treated with Pharmacia FPLC system using a Mono Q column eluting with a linear gradient of 0 to 0.5 M potassium chloride in buffer A, gave the objective purified enzyme of 30 to 60 units.

Figure 11:
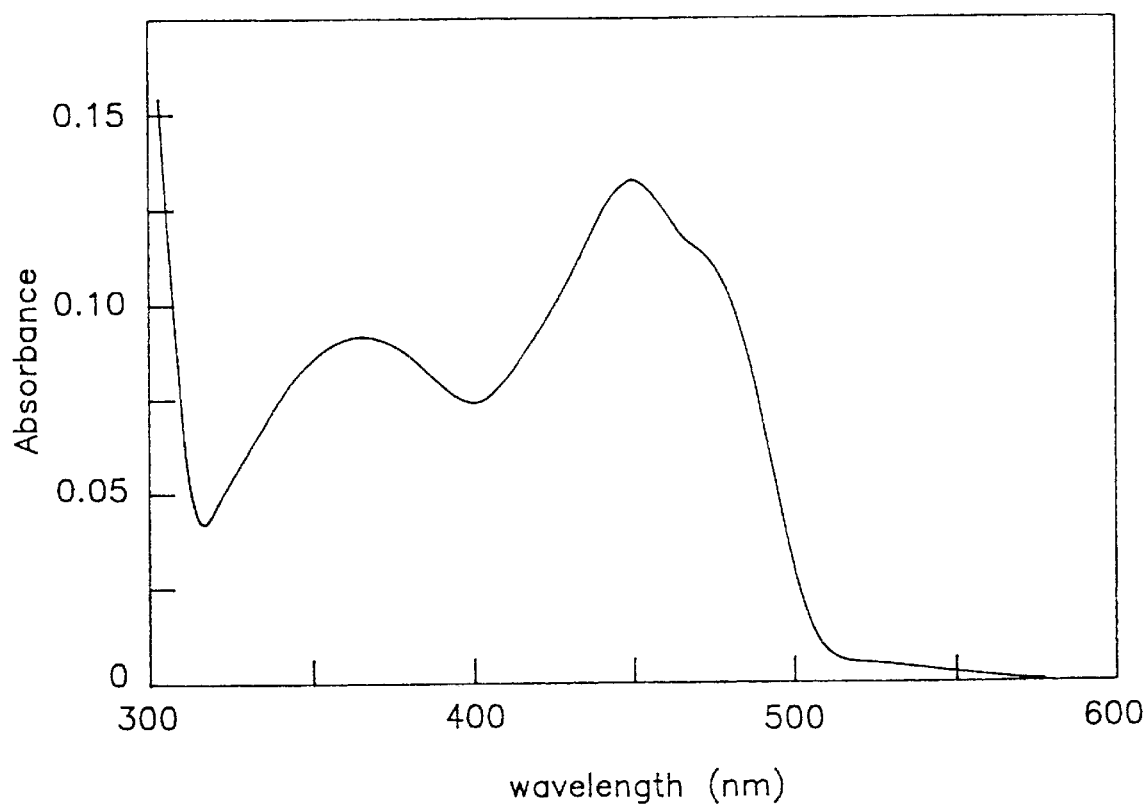
FIG. 11 shows absorption spectrum of a purified FLOD-S derived from S-1F4 strain.

UV absorption spectrum of the purified enzyme is shown in FIG. 11. FIG. 11 suggests that this enzyme is a flavin enzyme.

The purified enzyme was used for determination of molecular weight by column gel filtration on Sephacryl S-200 and by SDS-PAGE (sodium dodecylsulfate polyacrylamide gel electrophoresis). The column chromatography was conducted using 0.1 M Tris-HCl buffer (pH 8.5) containing 0.1 M NaCl, and molecular weight was estimated using several standards of known proteins, which were treated in the same manner, on the basis of the elution volume.

Figure 5:
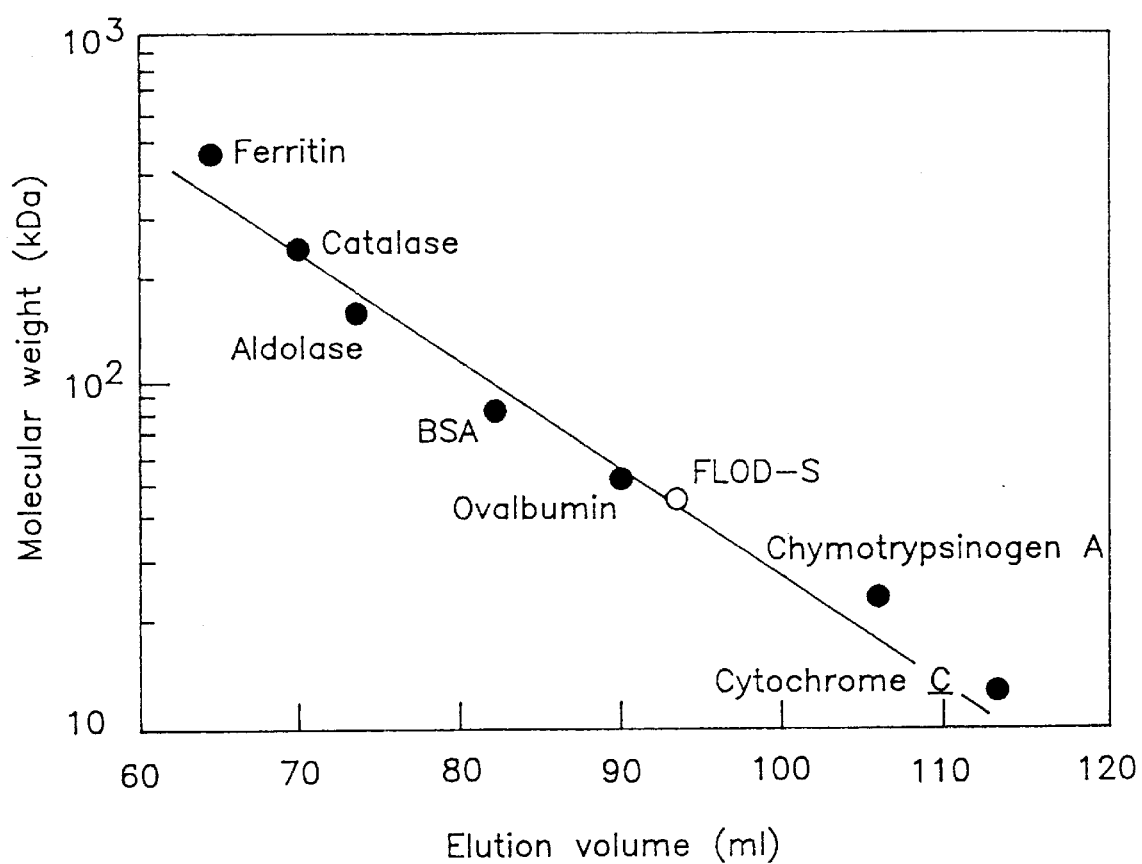
FIG. 5 is a graph illustrating the results of the determination of molecular weight of FLOD-S derived from S-1F4 strain by means of gel filtration using Sephacryl S-200.
Figure 6:
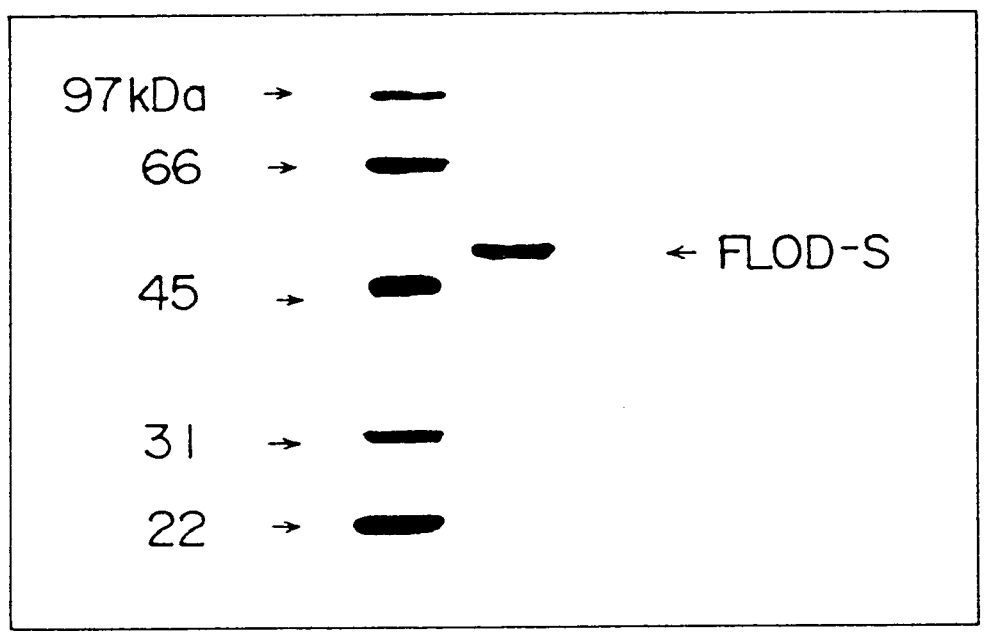
FIG. 6 shows the migration pattern obtained by subjecting purified FLOD-S derived from S-1F4 to SDS-PAGE.
Figure 7:
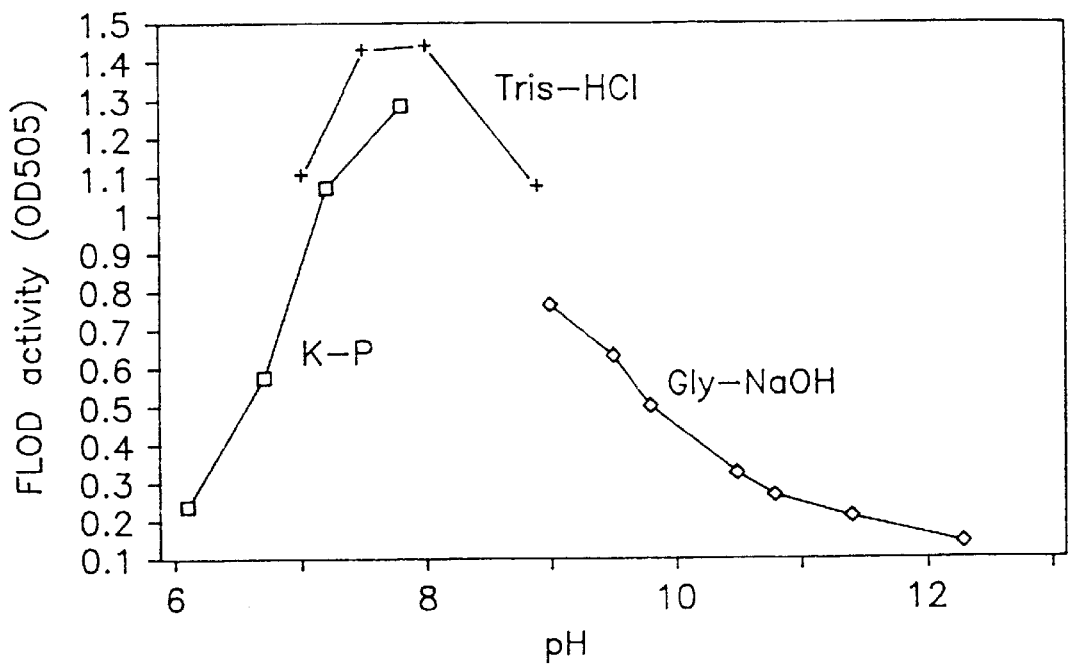
FIG. 7 is a graph illustrating a relation between the pH and the activity of FLOD-G derived from Gibberella in a solvent.
Figure 8:
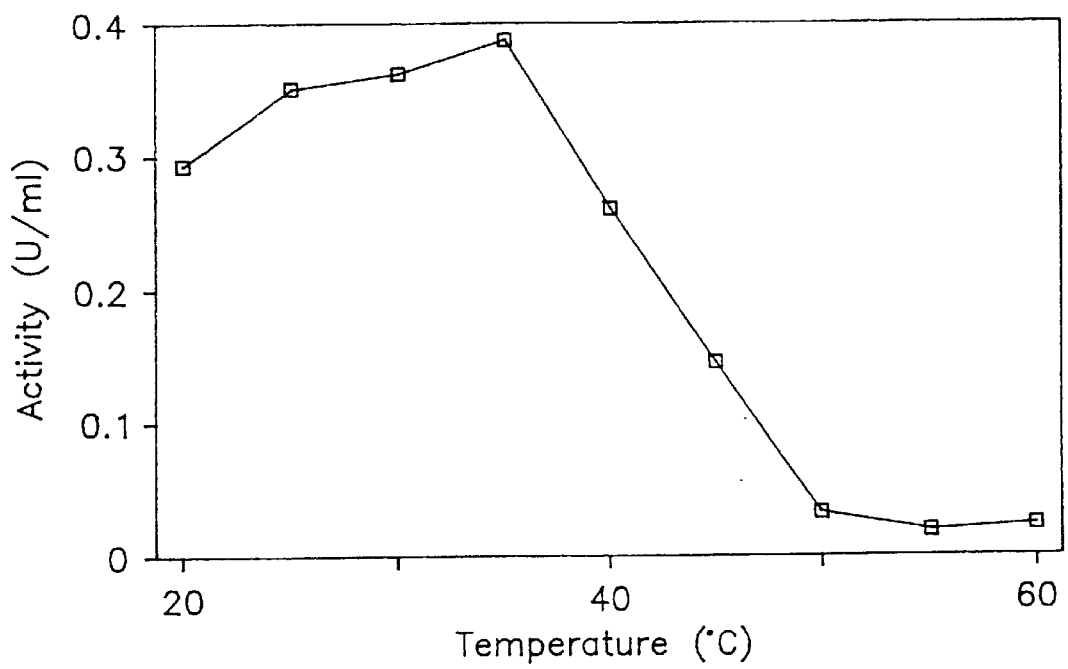
FIG. 8 is a graph illustrating a relation between the temperature and the activity of FLOD-G derived from Gibberella in a solvent.

SDS-PAGE was conducted according to a Davis's method (40 mA, 3 hours, and 10% gel). Protein was stained with Coumassie brilliant blue G-250. Molecular weight was estimated using several standards of known proteins, which were treated in the same manner, using a calibration curve. The determination revealed that the molecular weight of FLOD-S derived from S-1F4 is about 45,000 on column gel filtration using Sephacryl S-200, and about 50,000 on SDS-PAGE (see, FIGS. 5 and 6).

Furthermore, FLOD-S prepared in Example 1 showed the same values or physicochemical properties in connection with enzyme activity, pH and temperature stability, effect of metal and inhibitors and the like as those described in (I) above.

An assay was conducted, as shown in Example 2, using as a substrate, glycated human serum albumin (Sigma) having lysine residue attached to glucose [J. Biol. Chem. 26: 13542–13545 (1986)] and the purified FLOD-S prepared in Example 1 above.

EXAMPLE 2

Determination of the Amount of Glycated Albumin

1) Trypsin treatment Reagents used are as follows:

A: 2% trypsin solution in 0.1 M Tris-HCl buffer (pH 8.0);

B: aqueous 45 mM 4-aminoantipyrine solution;

C: 60 mM N-ethyl-N-(2-hydroxy-3-sulfopropyl)-m-toluidine;

D: peroxidase solution (60 units/ml); and

E: FLOD-S solution (14 units/ml)

FLOD-S solution (14 units/ml) in item E was prepared by diluting the purified FLOD derived from *F. oxysporum* S-1F4 obtained in Example 1 with distilled water to the concentration of 14 units/ml.

The FLOD reaction solution was prepared by mixing 1 ml each of solutions B to E and 10 ml of 0.1 M Tris-HCl buffer (pH 8.0) and adjusting the volume to 30 ml with distilled water.

Trypsin treatment was conducted by incubating a mixture obtained by combining 30 μl of glycated human serum albumin (Sigma Co.) of various concentrations (0 to 1.0%) with an equal amount of solution A at 37° C. for 60 minutes.

2) Determination

To the trypsin-treated solution was added 1 ml of FLOD reaction solution and incubated at 30° C. for 30 minutes. Then, absorbance at 555 nm was measured.

Figure 12:
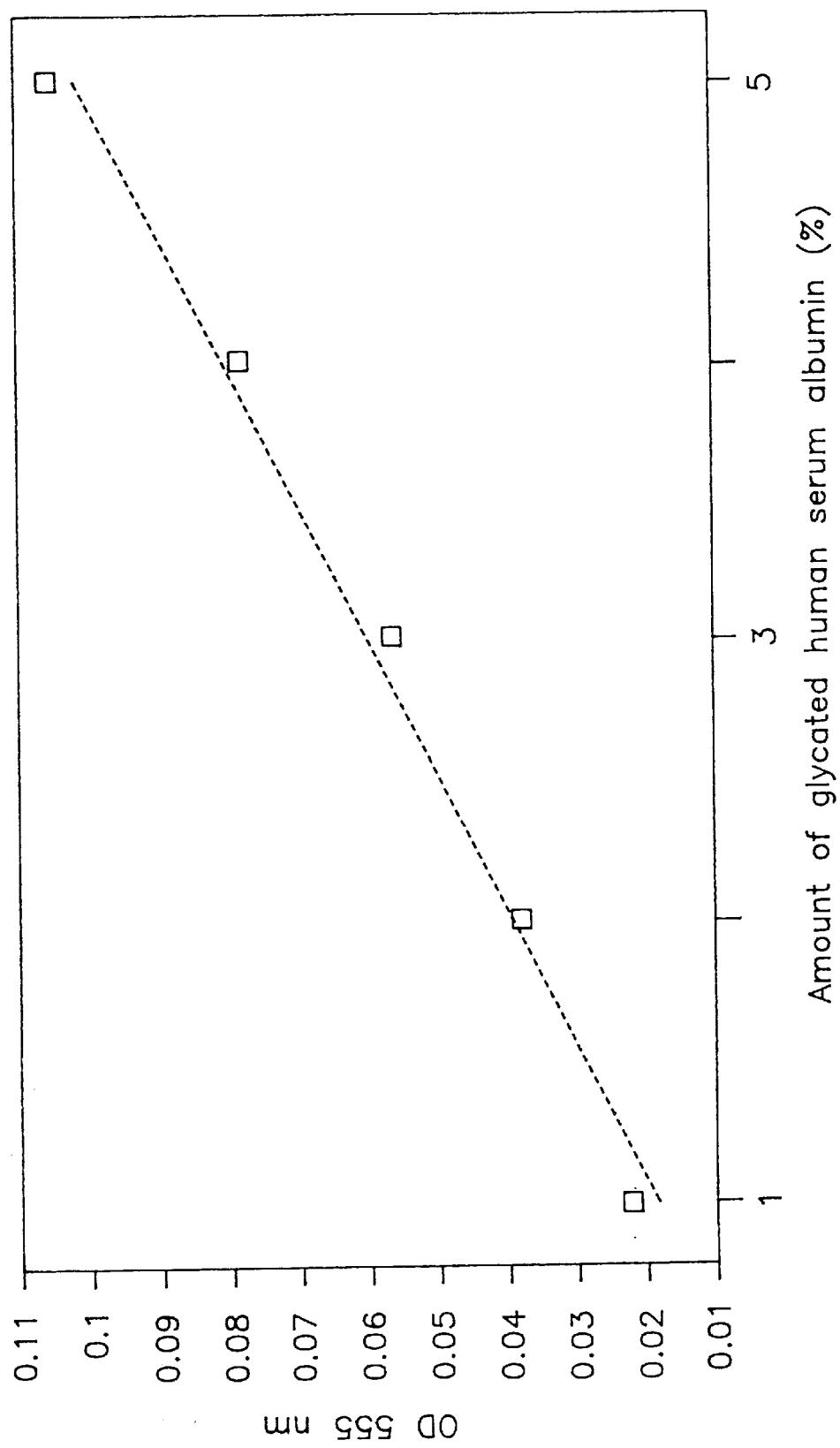
FIG. 12 is a graph illustrating a relation between the concentration of glycated human serum albumin as a substrate and the amount of hydrogen peroxide produced by FLOD-S.

The results are shown in FIG. 12. In FIG. 12, the ordinate indicates the absorbance at 555 nm which corresponds to the amount of hydrogen peroxide generated and the abscissa the concentration of glycated albumin. FIG. 12 indicates that the concentration of the glycated albumin and the amount of hydrogen peroxide are correlated.

EXAMPLE 3

Measurement of Glycation Rate of Human Serum Albumin

Each of 150 mg of glycated human serum albumin (Sigma Co.) and 150 mg of human serum albumin (Sigma Co.) was dissolved in 3 ml of aqueous 0.9% sodium chloride solution. The two solutions were combined to prepare solutions of different glycation rate and assay was carried out using an automatic glycoalbumin measuring device (Kyoto Daiichi Kagaku Co.). The measurement revealed that the glycation rate is from 24.1 to 51.9%.

Solutions of different glycation rate were used to prepare pre-treated sample solutions each comprising the following ingredients:

190 μl of glycated albumin solution;

20 μl of 6 mg/ml proteinase K (Sigma Co.);

20 μl of 6 mg/ml pronase E (Sigma Co.); and

20 μl of 1.25% SDS.

The mixture was incubated at 55° C. for 30 minutes to obtain a pre-treated sample solution.

Thereafter, a portion of each solution was taken and added to a reaction solution comprising the following ingredients:

70 μl of 45 mM 4-aminoantipyrine solution;

70 μl of 60 mM phenol solution;

70 μl of peroxidase solution (60 units/ml);

700 μl of 0.1 M Tris-HCl buffer (pH 8.0); and

30 μl of FLOD-S solution (11.5 units/ml).

Distilled water was added to a total volume of 2 ml.

The FLOD-S solution (11.5 units/ml) was prepared by diluting FLOD-S prepared in the same manner as that described in Example 1 with 0.1 M Tris-HCl buffer (pH 8.0) to a concentration of 11.5 units/ml.

Figure 13:
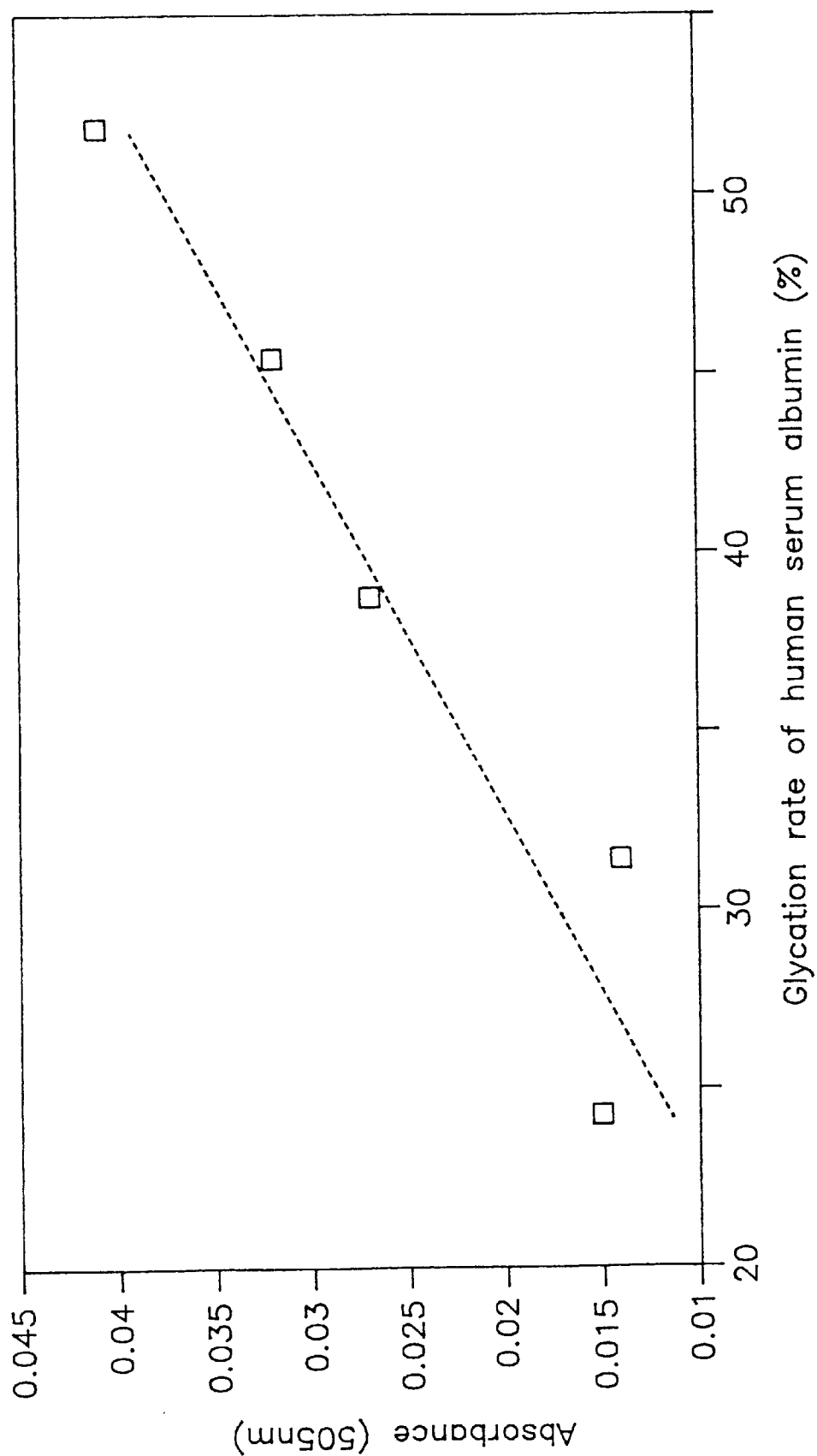
FIG. 13 is a graph illustrating a relation between the glycation rate of albumin and the amount of hydrogen peroxide produced by FLOD-S.

After this reaction solution was incubated at 30° C., 100 μl each of the pre-treated sample solutions was added thereto and absorbance at 505 nm after 30 minutes was measured. The relation between the glycation rate of albumin and the absorbance is shown in FIG. 13. In FIG. 13, the ordinate indicates the absorbance at 505 nm which corresponds to the amount of hydrogen peroxide produced and the abscissa the glycation rate of albumin. FIG. 13 indicates that the glycation rate of albumin is correlated with the amount of hydrogen peroxide produced.

EXAMPLE 4

Determination of Glycated Protein in Blood

Figure 14:
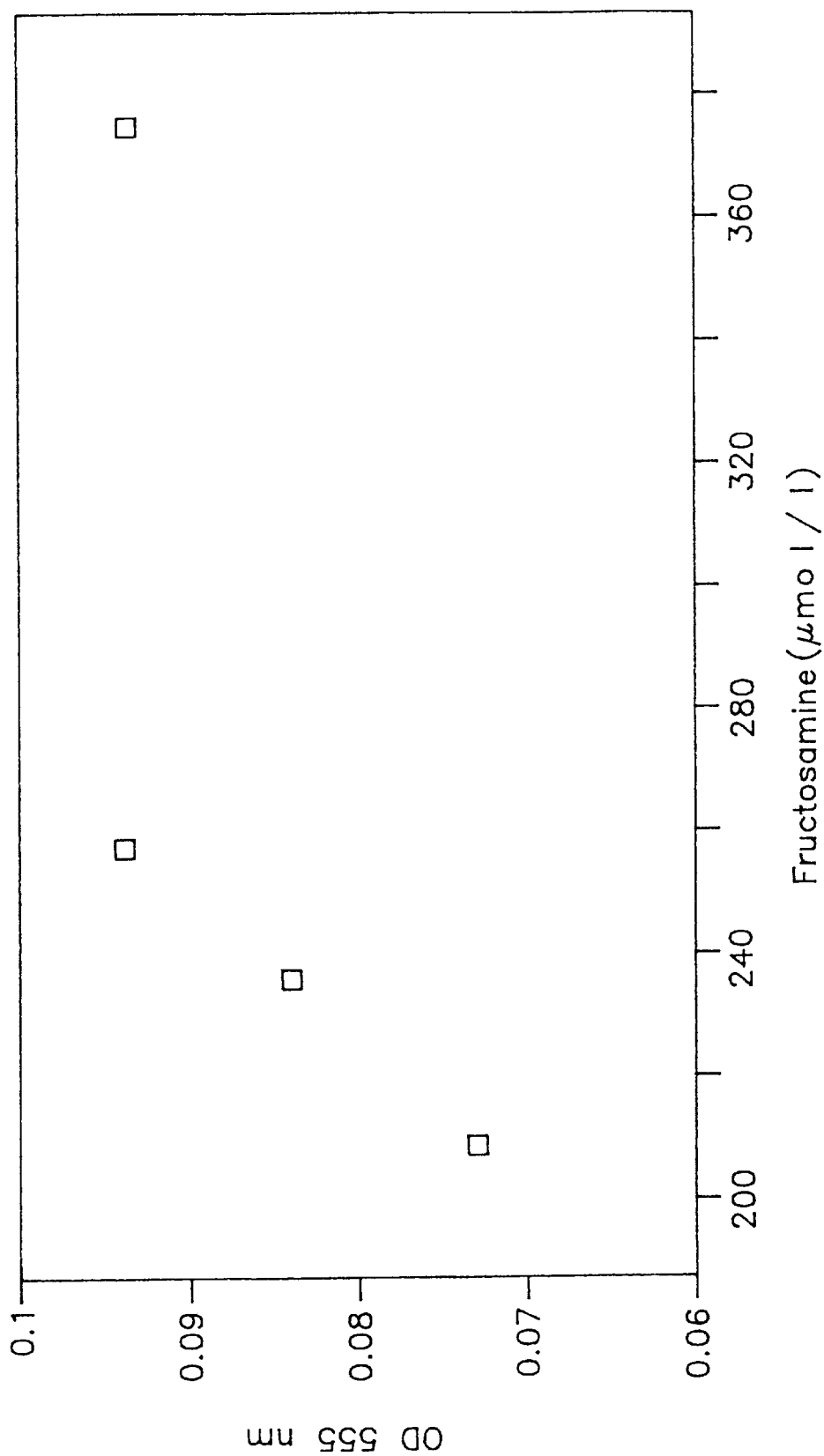
FIG. 14 is a graph illustrating a relation between the fructosamine level in serum derived from a diabetic and the concentration of glycated protein obtained using FLOD-S.
Figure 15:
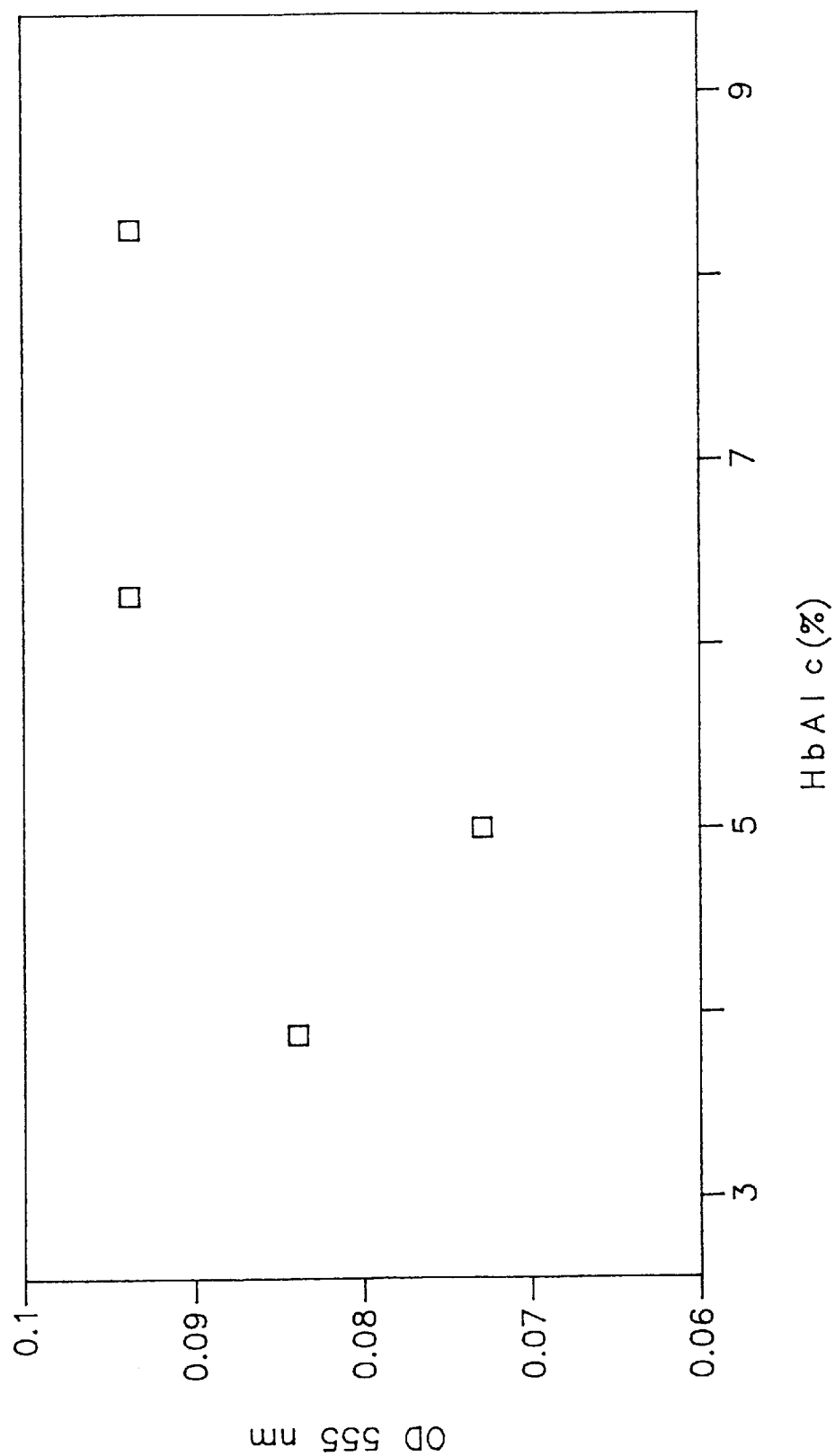
FIG. 15 is a graph illustrating a relation between the hemoglobin A1c level in whole blood derived from a diabetic and the concentration of the glycated protein obtained using FLOD-S.

Glycated protein in blood from a diabetic was assayed according to the same manner as that described in Example 2 using diabetic's serum as the substrate and FLOD purified in Example 1. Fructosamine value in serum or a hemoglobin A1c level in total blood has been used as an index for control of diabetes. In the present Example, the relation between the results of enzymic assay of glycated protein (serum albumin) using FLOD-S of the present invention and the indices conventionally used in the control of diabetes was evaluated using blood samples derived from diabetic outpatients. The results are shown in FIGS. 14 and 15. In these Figures, the ordinate indicates the absorbance at 555 nm which corresponds to the amount of hydrogen peroxide produced and the abscissa the fructosamine value in patient's serum (FIG. 14), or the hemoglobin A1c level in whole blood (FIG. 15). FIGS. 14 and 15 indicate that the results of assay of glycated protein using FLOD-S are correlated with indices conventionally used in the control of blood glucose level of diabetic, demonstrating that the method of the present invention is useful to obtain an index of diabetes.

Patients showing high HbA1c and/or fructosamine level are considered to show high glycated protein (serum albumin) level. Fructosamine being produced through the glycation of serum protein, it is in well correlation with the in vivo life span of albumin which is the main ingredient of serum proteins. As to HbA1c, the mutual relation between HbA1c and glycated protein is expected to be lower than that between fructosamine and glycated protein because the in vivo life span of hemoglobin differs from that of albumin and that the glycation site of HbA1c is valine residue. This can be seen from FIGS. 14 and 15.

EXAMPLE 5

Preparation and Purification of FLOD-G

Derived from *G fujikuroi* (IFO No. 6356, FERM BP-5982) *Gibberella fujikuroi* (IFO No. 6356, FERM BP-5982) was inoculated into a medium (pH 6.0, 10 L) containing 0.5% FZL, 1.0% glucose, 0.1% dipotassium phosphate, 0.1% monosodium phosphate, 0.05% magnesium sulfate, 0.01% calcium chloride and 0.2% yeast extract, and grown at 28° C. for 24 hours with aeration (2 L/min) and stirring (400 rpm) using a jar fermentor. The culture was filtered to harvest mycelia. A portion of mycelia (200 g) was suspended in 0.1 M Tris-HCl buffer (pH 8.5, 1 L) containing 2 mM DTT and ground with Dino-Mill. The ground mixture was centrifuged at 10,000 rpm for 15 minutes to give a crude enzyme solution. To the crude enzyme solution was added ammonium sulfate to 40% saturation and the mixture was stirred and centrifuged at 12,000 rpm for 10 minutes. To the supernatant was added ammonium sulfate to 75% saturation and the mixture was stirred and centrifuged at 12,000 rpm for 10 minutes. The precipitates were dissolved in 50 mM Tris-HCl buffer (pH 8.5) containing 2 mM DTT (hereinafter, referred to as "buffer A") and the solution was dialyzed overnight against the buffer A. The dialyzed substance was adsorbed onto DEAE-Sephacel column equilibrated with the buffer A. After washing with the buffer A, the column was eluted with a linear gradient of 0 to 0.5 M potassium chloride. The active fractions were collected and fractionated with ammonium sulfate ranging from 55 to 75%, followed by overnight dialysis against the buffer A. To the dialyzed substance was added ammonium sulfate to 25% saturation, which substance was then adsorbed onto a phenyl-Toyopearl column equilibrated with the buffer A containing 25% ammonium sulfate. After washing with the same buffer, the column was eluted with a linear gradient of 25 to 0% saturation of ammonium sulfate. The active fractions were collected. After addition of ammonium sulfate to 40% saturation, the solution was adsorbed onto a butyl-Toyopearl column equilibrated with the buffer A containing 40% saturated ammonium sulfate. After washing with the same buffer, the column was eluted with a linear gradient of 40 to 0% saturation of ammonium sulfate. The active fractions were collected. To the solution was added ammonium sulfate to 80% saturation. The mixture was stirred and centrifuged at 12,000 rpm for 10 minutes. The precipitates were dissolved in 0.1 M buffer A to give an enzyme solution. The enzyme solution was subjected to gel filtration chromatography using Sephacryl S-200 equilibrated with buffer A containing 0.1 M potassium chloride. The active fractions were collected and concentrated by means of ultrafiltration. The concentrate, when treated with Pharmacia FPLC system using a Mono Q column eluting with a linear gradient of 0 to 0.5 M potassium chloride in buffer A, gave the objective purified enzyme of 30 to 60 units.

Figure 10:
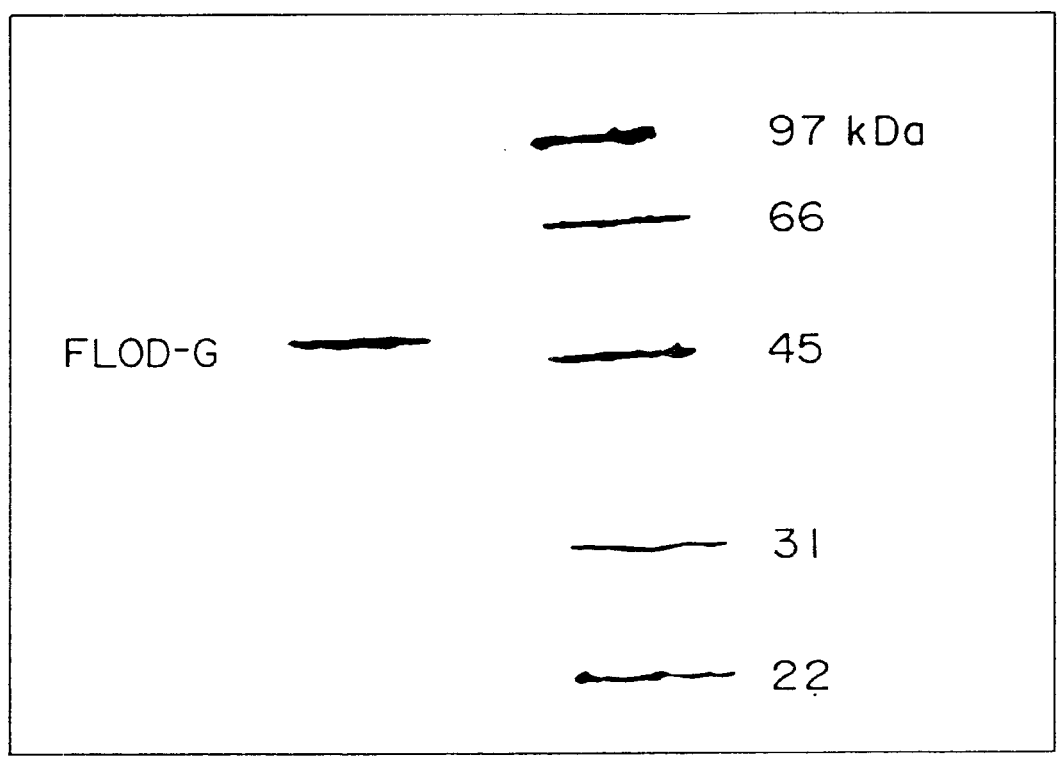
FIG. 10 shows the migration pattern obtained by subjecting FLOD-G derived from Gibberella to SDS-PAGE.

The resultant purified enzyme preparation was for determination of molecular weight by SDS-PAGE using several standards of known proteins such as phosphorylase B, bovine serum albumin (BSA), ovalbumin, carbonic anhydrase and soybean trypsin inhibitor. Specifically, SDS-PAGE was conducted according to a Davis's method (40 mA, 3 hours, 10% gel) and protein was stained with Coumassie brilliant blue G-250. Molecular weight of a subunit referring to a calibration curve, was about 52,000 (52 kDa) (see, FIG. 10).

Figure 9:
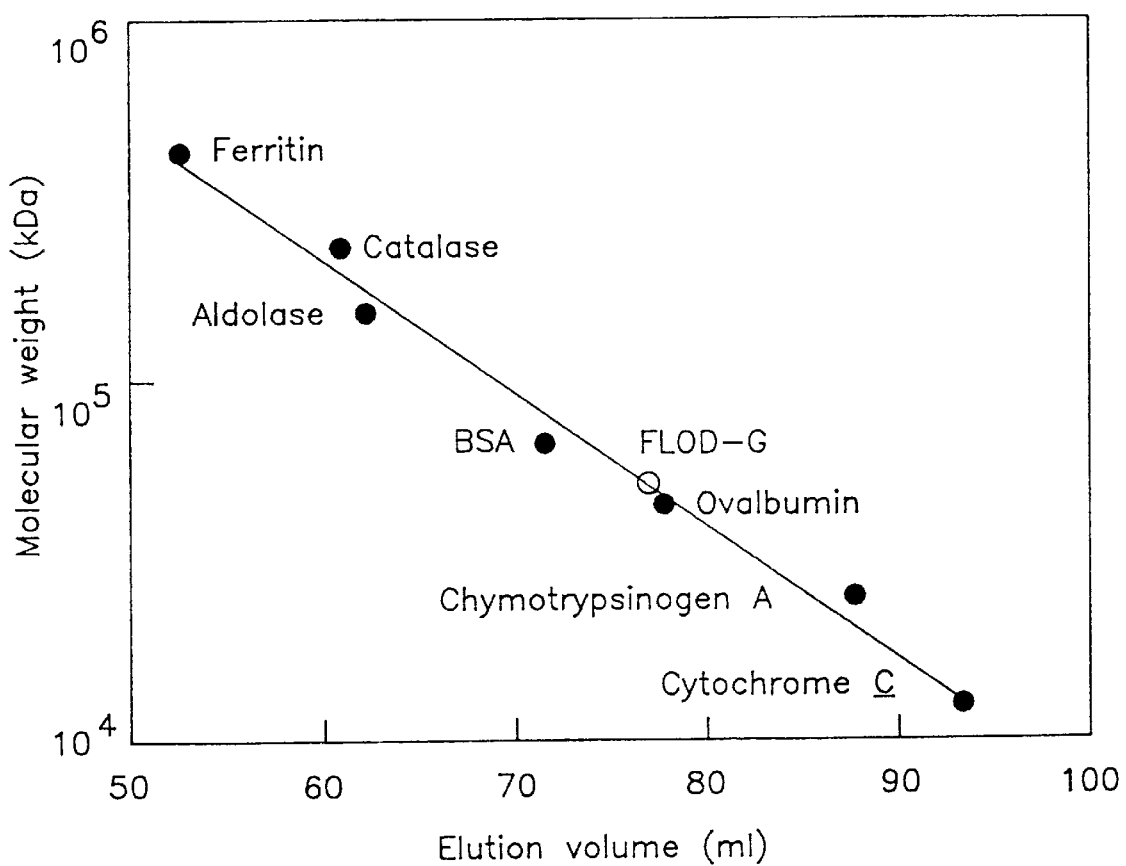
FIG. 9 is a graph obtained by subjecting FLOD-G derived from Gibberella to gel filtration on Superdex 200 pg.

When estimated by gel filtration on Superdex 200 pg, molecular weight was about 47,000 (47 kDa) as is apparent from the calibration curve in FIG. 9.

Furthermore, FLOD-G prepared in Example 5 showed similar values or physicochemical properties in connection with enzyme activity, pH and temperature stability, effect of metal and inhibitors and the like to those described in respective item in (II) above.

EXAMPLE 6

Determination of Fructosyl Poly-lysine

A 0.1% fructosyl poly-lysine solution which had proved to contain 750 μmol/l fructosamine by BMY NBT assay was used. A series of sample solutions each containing fructosamine at a concentration ranging from 0 to 750 μmol/l was prepared by diluting this solution.

Each diluted solution was mixed with an equal amount of 0.05% trypsin and incubated at 37° C. for one hour to obtain a pre-treated sample. Thereafter, a portion of each sample was taken and added to a reaction solution comprising the following ingredients:

50 μl of 45 mM 4-aminoantipyrine solution;
50 μl of 60 mM phenol solution;
50 μl of peroxidase solution (60 units/ml);
500 μl of 0.1 M Tris-HCl buffer (pH 8.0); and
30 μl of FLOD-G solution (7.6 units/ml).

Distilled water was added to a total volume of 1300 μl.

The FLOD-G solution (7.6 units/ml) was prepared by diluting FLOD-G obtained in the same manner as that described in Example 5 with 0.1 M Tris-HCl buffer (pH 8.0) to a concentration of 7.6 units/ml.

Figure 16:
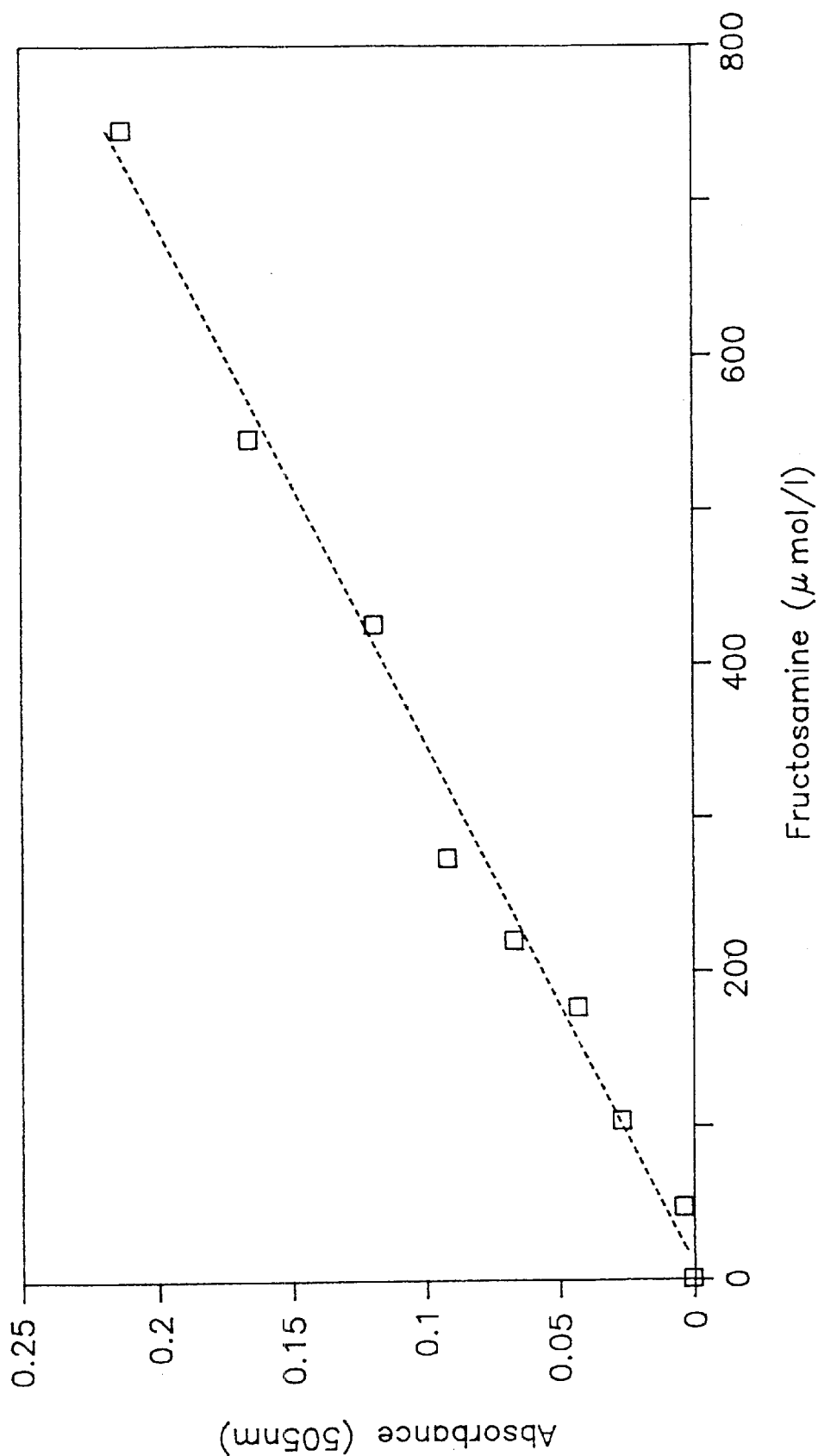
FIG. 16 is a graph illustrating a relation between the concentration of fructosamine and the amount of hydrogen peroxide produced by PLOD-G.

After this reaction solution was incubated at 30° C., 200 μl each of the treated sample solutions was added thereto. Absorbance at 505 nm after 30 minutes was measured. The relation between the fructosamine value and the absorbance obtained by this method is shown in FIG. 16. In FIG. 16, the ordinate indicates the absorbance at 505 nm which corresponds to the amount of hydrogen peroxide and the abscissa the fructosamine value. FIG. 16 indicates that the fructosamine value is correlated with the amount of hydrogen peroxide generated.

EXAMPLE 7

Measurement of Glycation Rate of Human Serum Albumin

Each of 150 mg of glycated human serum albumin (Sigma Co.) and 150 mg of human serum albumin (Sigma Co.) was dissolved in 3 ml of aqueous 0.9% sodium chloride solution. The two solutions were combined to prepare solutions of different glycation rate and assayed using an automatic glycoalbumin measuring device (Kyoto Daiichi Kagaku Co.). The measurement revealed that the glycation rate is from 24.1 to 51.9%.

Solutions of different glycation rate were used to prepare pre-treated sample solutions each comprising the following ingredients:

190 μl of glycated albumin solution;
20 μl of 6 mg/ml proteinase K (Sigma Co.);
20 μl of 6 mg/ml pronase E (Sigma Co.); and
20 μl of 1.25% SDS.

The mixture was incubated at 55° C. for 30 minutes to obtain a pre-treated sample solution. Thereafter, a portion of each solution was taken and added to a reaction solution comprising the following ingredients:

70 μl of 45 mM 4-aminoantipyrine solution;
70 μl of 60 mM phenol solution;
70 μl of peroxidase solution (60 units/ml);
700 μl of 0.1 M Tris-HCl buffer (pH 8.0); and
30 μl of FLOD-G solution (7.6 units/ml).

Distilled water was added to a total volume of 2 ml.

Figure 17:
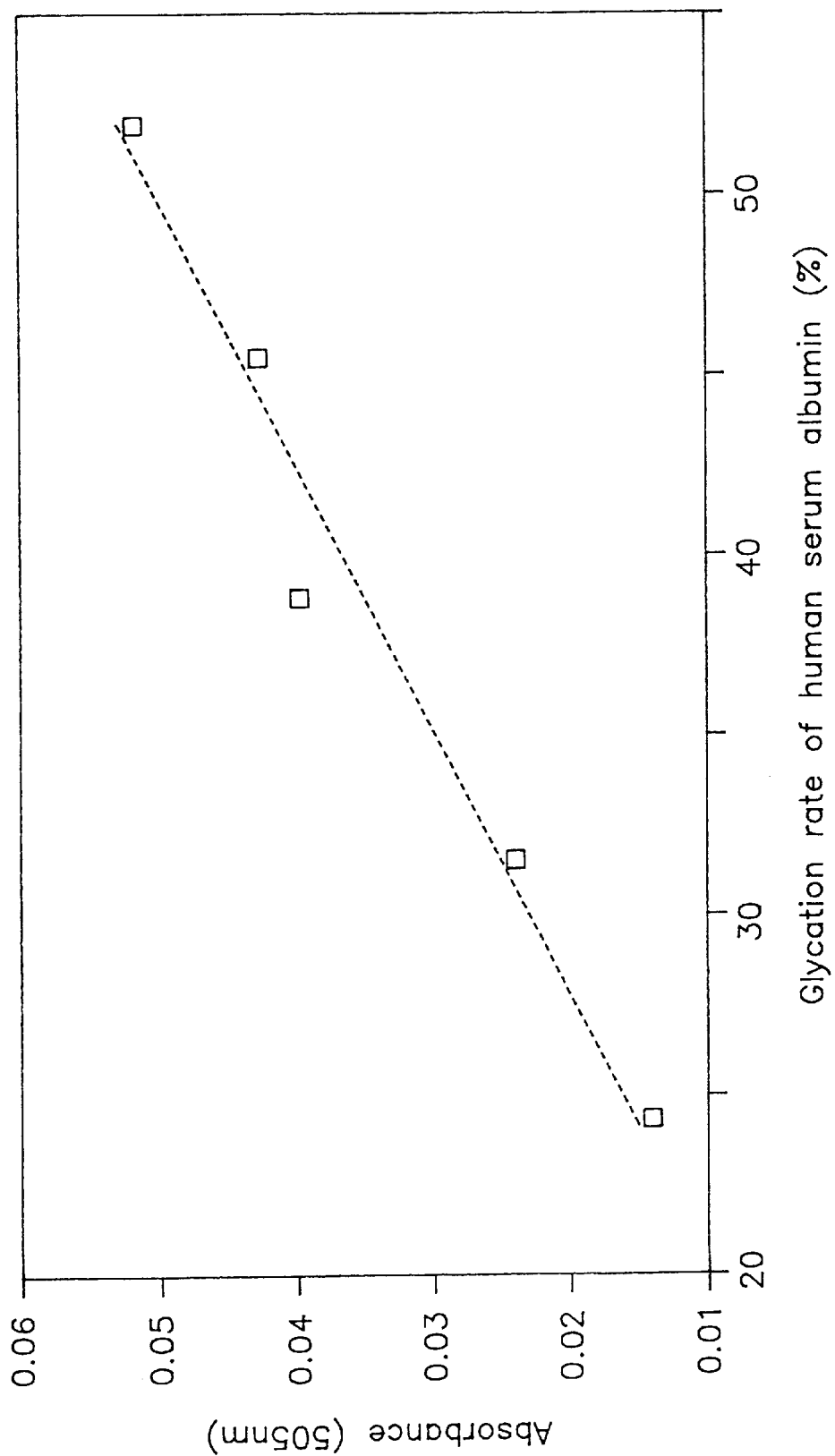
FIG. 17 is a graph illustrating a relation between the glycation rate and the amount of hydrogen peroxide produced by FLOD-G.

After this reaction solution was incubated at 30° C., 100 μl each of the pre-treated sample solutions were added thereto. Absorbance at 505 nm after 30 minutes was measured. The relation between the glycation rate of albumin and the absorbance is shown in FIG. 17. In FIG. 17, the ordinate indicates the absorbance at 505 nm which corresponds to the amount of hydrogen peroxide and the abscissa the glycation rate of albumin. FIG. 17 indicates that the glycation rate of albumin is correlated with the amount of hydrogen peroxide generated.

What is claimed is:

1. A purified fructosyl amino acid oxidase originated from a strain of Fusarium, having the following physicochemical characteristics:

1) catalyzes the oxidation of an amadori compound, in the presence of oxygen, to generate α-ketoaldehyde, amine derivatives and hydrogen peroxide;

2) catalyzes the oxidation of a substance comprising a lysine residue that is glycated at the ε-position, in the presence of oxygen, to generate α-ketoaldehyde, amine derivatives and hydrogen peroxide;

3) stable in the pH range of 4.0 to 12.0 and having optimum catalytic activity at pH 8.0;

4) stable in the temperature range of 20 to 55° C. and having optimum catalytic activity temperature 45° C.;

5) the molecular weight is from 45,000 daltons to 47,000 daltons when determined by gel filtration chromatography; and 6) the specific activity utilizing a fructosyl amino acid as a substrate is at least 20-fold higher than the specific activity utilizing a polymer of said fructosyl amino acid as a substrate.

2. The fructosyl amino acid oxidase of claim 1, which is obtained by culturing a strain of Fusarium, said strain producing a fructosyl amino acid oxidase, in a fructosyl-lysine-containing medium obtained by autoclaving a solution containing glucose together with $N^{\alpha}$-Z-lysine.

3. The fructosyl amino acid oxidase of claim 2, wherein the fructosyl-lysine-containing medium is obtained by autoclaving glucose together with $N^{\alpha}$-Z-lysine at 100 to 150° C. for 3 to 60 minutes.

4. The enzyme of claim 1, wherein the strain of Fusarium is *Fusarium oxysporum* S-1F4 (FERM BP-5010).

5. The fructosyl amino acid oxidase of claim 1, wherein the specific activity utilizing a fructosyl amino acid as a substrate is about 43-fold higher than the specific activity utilizing a polymer of said fructosyl amino acid as a substrate.

6. An isolate of the fungus *Fusarium oxysporum* S-1F4 deposited as FERM BP-5010.

* * * * *